(12) United States Patent
Rovekamp, Jr. et al.

(10) Patent No.: US 12,740,882 B2
(45) Date of Patent: Sep. 22, 2026

(54) WEARABLE AUTOTENSIONING DEVICE

(71) Applicants: Roger Neil Rovekamp, Jr., Kemah, TX (US); Keith Sawmiller, Beavercreek, OH (US)

(72) Inventors: Roger Neil Rovekamp, Jr., Kemah, TX (US); Keith Sawmiller, Beavercreek, OH (US)

(73) Assignee: Cincinnati Automation & Mechatronics LLC, Beavercreek, OH (US)

( * ) Notice: Subject to any disclaimer, the term of this patent is extended or adjusted under 35 U.S.C. 154(b) by 762 days.

(21) Appl. No.: 17/910,630

(22) PCT Filed: Mar. 12, 2021

(86) PCT No.: PCT/US2021/022144
§ 371 (c)(1),
(2) Date: Sep. 9, 2022

(87) PCT Pub. No.: WO2021/183909
PCT Pub. Date: Sep. 16, 2021

(65) Prior Publication Data

US 2023/0137746 A1 May 4, 2023

Related U.S. Application Data

(60) Provisional application No. 63/008,031, filed on Apr. 10, 2020, provisional application No. 62/988,508, filed on Mar. 12, 2020.

(51) Int. Cl.
*A61F 5/01* (2006.01)
*F16B 2/08* (2006.01)
*G05D 15/01* (2006.01)

(52) U.S. Cl.
CPC .............. *A61F 5/0102* (2013.01); *F16B 2/08* (2013.01); *G05D 15/01* (2013.01)

(58) Field of Classification Search
CPC .......... A61F 5/0102; F16B 2/08; G05D 15/01
See application file for complete search history.

(56) References Cited

U.S. PATENT DOCUMENTS 3,258,214 A * 6/1966 Comstock .............. G11B 15/43 242/417.3
6,146,312 A * 11/2000 Schlichter ............ A63B 23/0244 482/4

(Continued)

FOREIGN PATENT DOCUMENTS

CN 101961161 A 2/2011
WO WO 2019238231 A1 12/2019

OTHER PUBLICATIONS

EP21767058.7 Extended Search Report dated Mar. 5, 2024.

*Primary Examiner* — Jason W San
*Assistant Examiner* — Matthew J Sullivan
(74) *Attorney, Agent, or Firm* — Woodard Emhardt Henry Reeves & Wagner LLP

(57) ABSTRACT

An apparatus for automatically adjusting tension on a retention member and thereby applying compression or other forces to an object. Sensors may be used to sense changes associated with the object involved or the environment, and an actuator may be included that automatically rotates a rotating member such as a gear or pulley to automatically adjust tension on the retention member. The adjustments in tension may be made performed automatically and many times per second based on control signals from control logic responsive to the sensors.

20 Claims, 16 Drawing Sheets

(56) References Cited

U.S. PATENT DOCUMENTS

| | | | | |
|---|---|---|---|---|
| 9,194,493 | B2 * | 11/2015 | Richiuso | F16B 2/18 |
| 9,610,185 | B2 * | 4/2017 | Capra | A61F 5/0102 |
| 9,677,541 | B2 * | 6/2017 | Fahrner | F03D 7/0208 |
| 9,928,713 | B2 * | 3/2018 | Baczuk | H04W 4/023 |
| 10,249,218 | B2 * | 4/2019 | Bronson | G09B 23/28 |
| 10,272,195 | B2 * | 4/2019 | Kamen | A61M 5/14244 |
| 10,363,046 | B2 * | 7/2019 | Hopman | A44B 11/266 |
| 10,458,580 | B2 * | 10/2019 | Henrich | F16B 2/08 |
| 10,939,835 | B2 * | 3/2021 | Aliamiri | A61B 5/0245 |
| 11,357,910 | B2 * | 6/2022 | Kamen | A61M 5/14244 |
| 12,070,574 | B2 * | 8/2024 | Kamen | G01F 11/08 |
| 12,144,757 | B2 * | 11/2024 | Miller | A61F 5/0125 |
| 2012/0071917 | A1 * | 3/2012 | McDonald | G01L 5/102<br>116/212 |
| 2014/0051938 | A1 * | 2/2014 | Goldstein | A61B 5/741<br>600/301 |
| 2014/0257156 | A1 * | 9/2014 | Capra | A43B 3/34<br>602/5 |
| 2016/0033994 | A1 | 2/2016 | Rothkopf et al. | |
| 2017/0312161 | A1 | 11/2017 | Johnson et al. | |
| 2018/0008449 | A1 * | 1/2018 | Feinstein | A41F 1/002 |
| 2018/0027931 | A1 | 2/2018 | Baranski et al. | |
| 2018/0310670 | A1 | 11/2018 | Rovecamp, Jr. et al. | |
| 2019/0142288 | A1 * | 5/2019 | Aliamiri | A61B 5/6885<br>600/301 |
| 2020/0029660 | A1 | 1/2020 | Wu et al. | |
| 2021/0290089 | A1 * | 9/2021 | Scardulla | A61B 5/02141 |
| 2023/0372186 | A1 * | 11/2023 | Rovekamp, Jr. | A61F 5/05816 |
| 2024/0140356 | A1 * | 5/2024 | Rings | B60R 22/343 |
| 2024/0268980 | A1 * | 8/2024 | Forsell | A61F 5/0069 |
| 2024/0299038 | A1 * | 9/2024 | Kuhnreich | A61B 17/1327 |
| 2025/0347360 | A1 * | 11/2025 | Berry | F16L 3/1058 |

* cited by examiner 700
701
702
707
710
709
704
706
707

800
803
801
802
804
805
801
806
807

1801
1802
1800
1803
1804
1811
1805
1812
1809
1806
1807
1810

2200
2201
2202
2203
2204
2205
2206

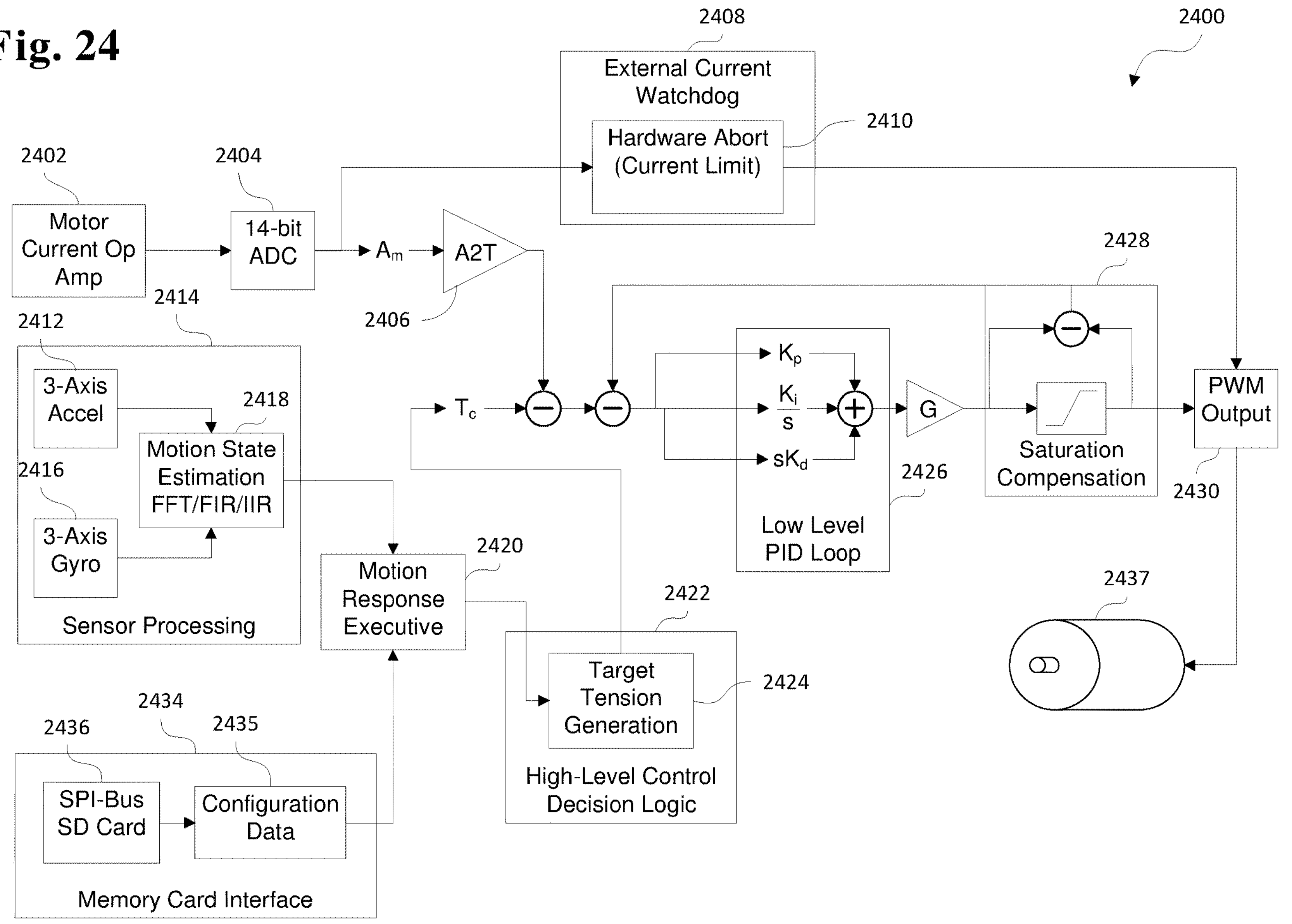
Fig. 24
2400
2408
External Current Watchdog
Hardware Abort (Current Limit)
2410
2402
Motor Current Op Amp
2404
14-bit ADC
$A_m$
A2T
2406
2414
2412
3-Axis Accel
2418
Motion State Estimation FFT/FIR/IIR
2416
3-Axis Gyro
Sensor Processing
$T_c$
$K_p$
$\frac{K_i}{s}$
$sK_d$
G
2426
Low Level PID Loop
2428
Saturation Compensation
PWM Output
2430
2437
Motion Response Executive
2420
2422
Target Tension Generation
2424
High-Level Control Decision Logic
2436
2434
2435
SPI-Bus SD Card
Configuration Data
Memory Card Interface

WEARABLE AUTOTENSIONING DEVICE

REFERENCE TO RELATED APPLICATION

The present application claims the benefit of U.S. Provisional Patent Application No. 62/988,508, filed Mar. 12, 2020, and U.S. Provisional Patent Application No. 63/008,031, filed Apr. 10, 2020, both of which are hereby incorporated by reference.

BACKGROUND

The present disclosure relates to wearable devices for automatically controlling tension applied to an object. In some instances, the optimum tension applied to the object may be dependent on movement of the object, movement of the wearable device relative to the object, environmental factors, or aspects of the state of the object itself. In many cases, tension may be set manually such as by tightening a strap, tying a shoe lace, twisting a wire or cable until it is “tight”, applying a locking or crimped cable stay, and the like. Such systems cannot determine an optimum level of tension, and/or cannot automatically adjust tension as needed. This can cause the tension level to be too high, thus damaging the tensioner itself, or damaging the object to be held in place by either applying too much tension, or by not applying enough.

SUMMARY

Disclosed is a wearable automatic retention apparatus for automatically adjusting tension on an object. The retention member may be separate and distinct from, and positionable around the object. The retention member may be arranged and configured to engage the object to increase or decrease tension on the object. A housing may be included that is optionally separate and distinct from the object, and the retention member may be mounted to the housing. An actuator may be mounted inside the housing that optionally includes a rotating member. The rotating member may be positioned to engage the retention member, and the rotating member may be rotatable around an axis of rotation in a first direction to increase tension on the retention member and in a second direction to decrease tension on the retention member. At least one sensor may be included that is optionally arranged and configured to sense changes in a sense parameter associated with the object.

In another aspect, a control circuit may be included that is responsive to input from the sensor and may be configured to control the actuator according to the input from the sensor. The control circuit may be configured to control the actuator to rotate the rotating member in the first or second direction to adjust tension on the retention member based on input from the sensor.

In another aspect, the rotating member optionally extends out of the housing to engage the retention member, and the retention member may be adjacent the housing to engage the rotating member accordingly. In another aspect, the rotating member may include a worm gear positioned adjacent to the retention member and optionally arranged and configured to engage holes or grooves defined by the retention member. In another aspect, the retention member is optionally rigid and may be wider than it is thick and may define one or more holes engageable by the worm gear.

In another aspect, an engagement portion of the retention member engages the rotating member inside the housing. In another aspect, the rotating member optionally includes a shaft and the engagement portion of the retention member may be configured to wind and unwind around the shaft in order to selectively increase or decrease tension on the object.

In another aspect, the retention member optionally includes a flexible substrate that may have a flat state and a curled state, the curled state of the flexible substrate may be suitable for conforming to the object. In another aspect, a first end of the retention member may be mounted to the housing, and a second end of the retention member may be selectively engageable with the rotating member when the flexible substrate is in the curled state. In another aspect, an engagement portion of the retention member may be configured to automatically engage the rotating member when the retention member is in the curled state. In another aspect, the control circuit may be configured to automatically activate the retention apparatus when the retention member is in the curled state. In another aspect, the flexible substrate may include, or be formed primarily of, a metallic bi-stable spring.

In another aspect, the automatic retention apparatus may include a frame mounted to the housing, and optionally at least one arm rotatably mounted to the frame. The retention member may be coupled to the arm, and the arm may be arranged and configured to rotate toward the object with increased tension on the retention member, to optionally rotate away from the object with decreased tension on the retention member. In another aspect, the arm may include multiple interconnected segments, and the retention member may be arranged to pass through the segments. The retention member may also be mounted to one of the multiple interconnected segments adjacent an end of the arm.

In another aspect, the disclosed retention apparatus may include a biasing element positioned adjacent to the rotating member, and the biasing element may be arranged and configured to bias the rotating member in a direction opposite the tension in the retention member. In another aspect, the biasing element may include a spring, and the element may share a common shaft with the rotating member.

In another aspect, the disclosed retention apparatus optionally includes a first rotating member and a second rotating member, and the first rotating member may be positioned to engage the retention member at a first end, and the second rotating member may be positioned to engage the retention member at a second end. The first and second rotating members may be rotatable in a first direction to increase tension on the retention member and/or in a second direction to decrease tension on the retention member.

In another aspect, the retained object may be a human or animal appendage, and the sense parameter may be any combination of blood pressure, body temperature, blood oxygen level, or heart rate. In another aspect, the control circuit is optionally configured to increase tension on the retention member when the sense parameter matches a first target criteria, and to optionally decrease tension on the retention member when the sense parameter matches a second target criteria. In another aspect, the disclosed retention apparatus may include an environment sensor arranged and configured to sense changes in an environmental sense parameter associated with the environment surrounding the sensor. The control circuit may be responsive to the environmental sense parameter which may include any combination of speed, angular momentum, velocity, movement, or acceleration. In another aspect, the environment sensor may be positioned in the housing.

In another aspect, an automatic retention system is disclosed for automatically adjusting tension on an object that optionally includes a frame, and multiple automatic retention apparatuses mounted to the frame. The multiple automatic retention apparatuses may be configured according to any of the disclosed examples. In another aspect, the automatic retention system of may include a frame with a joint, and at least one of the multiple automatic retention apparatuses may be mounted on one side of the joint, and at least one other of the multiple automatic retention apparatuses may be mounted on another side of the joint.

Further forms, objects, features, aspects, benefits, advantages, and examples of the present disclosure will become apparent from a detailed description and drawings provided herewith.

BRIEF DESCRIPTION OF THE DRAWINGS

FIG. 24 is a component flow diagram illustrating one example of a control circuit for controlling the automatic retention apparatus of the present disclosure.

DETAILED DESCRIPTION

Figure 1:
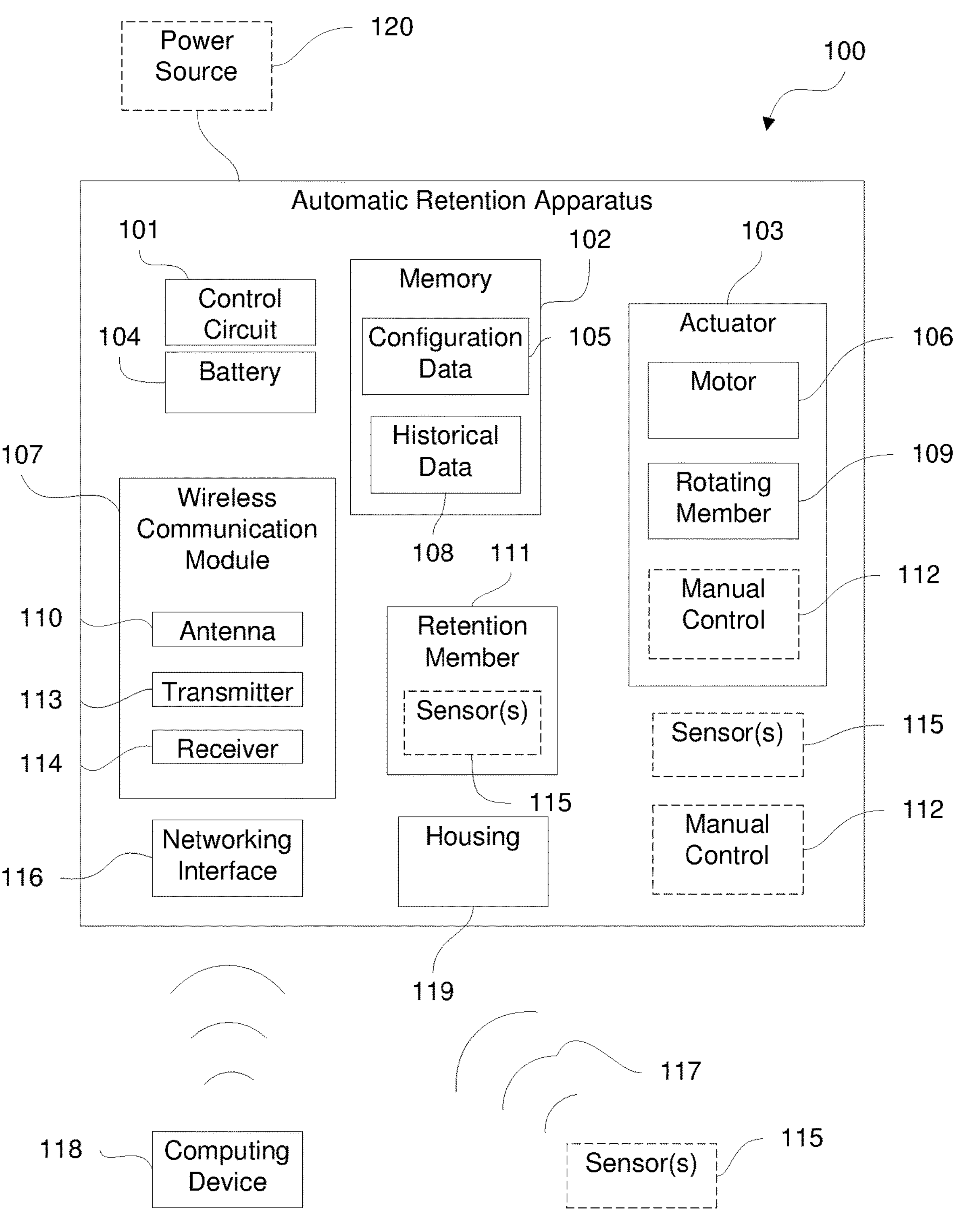
FIG. 1 is a component diagram illustrate one example of components that may be included in an automatic retention apparatus of the present disclosure.

FIG. 1 illustrates at 100 an example of components that may be included in the automatic retention apparatus of present disclosure. These components, and possibly others mentioned herein elsewhere, may be common to any or all of the disclosed examples of a retention apparatus.

An automatic retention apparatus 100 may include a control circuit 101 for processing data and generating commands or instructions to other components in the apparatus to control the operating behavior of the device. Control circuit 101 may include a processor, logic circuits, digital or analog circuitry, or any combination thereof, for accepting input and generating output for controlling operational characteristics of the apparatus 100. A battery 104 may be included for providing power to the control circuit 101, and to other components of the apparatus requiring electrical power. In another aspect, an optional external power source 120 may be included for providing power to the apparatus 100. This external power source 120 may be useful for charging battery 104, and/or for acting as a primary power source where battery 104 is uncharged or absent.

A memory 102 may be included for storing information such as configuration data 105 and historical data 108. In another aspect, memory 102 may be configured to store data such as time, direction, and extent of the rotation of the rotating member over a predetermined period of time. Data obtained over time from sensor input may also be stored in memory 102 for processing by control circuit 101, or for processing by other computing devices which may analyze the data to change configuration data 105 to improve the overall performance of the apparatus 100. Thus memory 102 may also be configured to store data values representing sense parameters detected by sensors 115 that was provided by the sensors as input to the control circuit 101. Historical data 108 may include dates, times, locations, or other metadata. Configuration data 105 may include parameter values for configuring the operation of the disclosed automatic retention apparatuses.

A wireless communication module 107 may be included and may include an antenna 110, transmitter 113, and receiver 114. The antenna may be used by the transmitter and receiver to send and receive wireless communications to a computing device 118 to, for example, send and receive updated configuration data, historical data, and/or control signals, or any combination thereof. Antenna 110 may be configured to resonate according to radio waves carrying signals defining data sent and received by wireless communication module 107. Transmitter 113 may use antenna 110 to send signals, and receiver 114 may also use antenna 110 to receive signals defining data to be processed by control circuit 101 and/or stored in memory 102. Signals sent and received by the transmitter and receiver may be sent via any suitable medium such as via radio waves, by modulating visible or invisible light, and the like.

A network interface 116 may be included and may implement various communication protocols useful for interacting with remote devices over a communications link that may be connected to a network such as the Internet. Such a communications link may be a wireless communications link implemented using wireless communication module 107, or a physical communication link implemented using wires, optical fibers, and the like. For example, wireless communication module 107 may transmit and receive signals which may then be processed according to the protocols recognized by network interface 116 in order to implement a communications link.

Retention apparatus 100 may include a retention member 111 for applying tension to an object. One or more sensors 115 may be included in or coupled to retention member 111. Sensors 115 may optionally be included in, or mounted to, retention member 111, or included in, or mounted to, automatic retention apparatus 100. In another aspect, sensors 115 may include sensors arranged and configured to sense changes in a sense parameter associated with an object retained by the device 100. In another aspect, sensors 115 may be included with or responsive to changes in sense parameters associated with the retention member 111. For example, sensors 115 may detect tension in the retention member thus allowing the control circuit to adjust the tension as needed.

In another aspect, sensors 115 may include environmental sensors arranged and configured to sense changes in an environmental sense parameter associated with an environment surrounding the sensor. These environmental sensors may be positioned in the housing 119, or elsewhere outside the housing. The control circuit 101 may be responsive to the environmental sense parameter as these parameters may represent any suitable environmental aspect such as speed, angular momentum, velocity, movement, acceleration, air pressure, heat or temperature, smoke, fire, humidity or the presence of liquid, depth in a fluid or body of water, altitude, attitude (that is, angle of inclination with respect to earth), or any combination thereof. Sensors 115 may be mounted to other objects interacting with apparatus 100 such as in the case of wireless sensors sending data received as signals 117 by wireless communication module 107 from a remote location.

An actuator 103 may be included and configured to act on retention member 111 to increase or decrease tension on the retention member to vary the resulting tension on any or objects to be held in place by retention member 111. A motor 106 may be included in actuator 103 and coupled to a rotating member 109 such as one ore more gears, cams, pulleys, and the like, or any combination thereof. An optional manual control 112 may be coupled to rotating member 109 to manually adjust the tension on retention member 111 by manually adjusting rotating member 109. This manual rotation may be performed along with, or as an alternative to, the automatic rotation provided by motor 106. In another aspect, the manual control 112 may be coupled to the retention member 111 separate from the actuator. Regardless of position, the tension or compression forces provided by the retention member may be manually adjusted using the manual control 112 along with, or as an alternative to, the automatic rotation provided by motor 106.

In another aspect, control circuit 101 may be responsive to input from at least one sensor of sensors 115 and may be configured to control the actuator accordingly. A control circuit may control the actuator instructing it to energize the motor to rotate the rotating member in the first or second direction to adjust automatically adjust tension on an object. For example, control circuit 101 may control the actuator to rotate in the first and second directions with the direction and number of rotations being a function of the input received from sensor 115. In another aspect, some or all of the components of 100 may be mounted to, or mounted inside, a housing 119. In another aspect, the control circuit 101 may be configured to increase tension on the retention member when the sense parameter matches a first target criteria, and/or to decrease tension on the retention member when the sense parameter matches a second target criteria.

Figure 2:
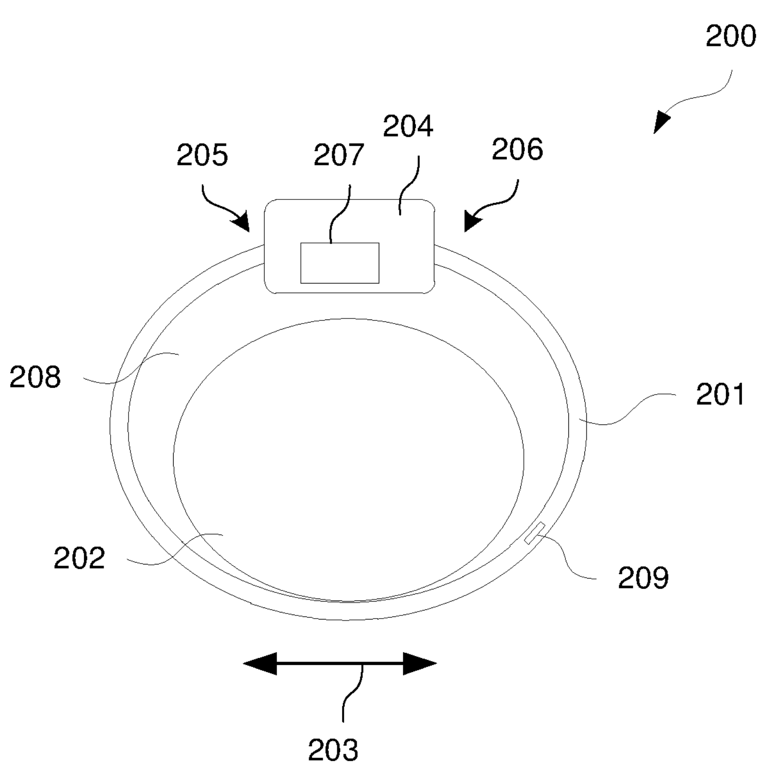
FIG. 2 is a component diagram illustrating aspects of an automatic retention apparatus of the present disclosure.

FIG. 2 illustrates additional aspects common to the disclosed automatic retention apparatuses as shown at 200. A retention member 201 is shown that is separate and distinct from an object 202. Retention member 201 is optionally positionable around the object 202, and the retention member arranged 201 is optionally arranged and configured to engage the object to increase or decrease tension on the object. In this example, retention member 201 may be rigid, or semi-rigid and therefore may be movable in the direction of 203. In this respect, retention member 201 may operate to apply tension by pulling toward the object 202, or alternatively by pushing toward the object 202. In another aspect, 201 may be flexible, or semi-flexible, thus allowing retention member 201 to only apply tension to the object by pulling toward the object 202.

In another aspect, retention member 201 may be mounted to a housing 204. In one example, retention member 201 may be mounted to housing 204 at, or adjacent to, a first end 205, a second end 206, or any combination thereof. In another aspect, the retention member 201 may engage an actuator 207 at, or adjacent to, the first or second ends 205 and 206. In another aspect, actuator 207 may engage retention member 201 at any point along its length.

In another aspect, the retention member 201 and the housing 204 together define an opening or empty space 208 within which object 202 may be positioned. For example, object 202 may be positioned such that retention member 201 is substantially perpendicular to the portion of object 202 that is positioned within the opening 208. However, any suitable orientation of object 202 with respect to the retention member 201 may be used.

In one nonlimiting example, object 202 may be a human or animal appendage, and retention member 201 may operate to automatically increase or decrease tension applied to the human or animal appendage. For example, retention apparatus 200 may automatically adjust tension of retention member 201 to increase or decrease pressure applied to the human or animal appendage, such as in the case of controlling a flow of blood or other bodily fluids at or adjacent to a wound.

In another aspect, a strain or compression sensor 209 may be included with or coupled to the retention member 201 to measure pressure on the object 202 as applied by the automatic retention apparatus. In another aspect, strain sensor 209 may be one of sensors 115 that is maintained adjacent to the retention member, and optionally separate from a housing or other portion of the apparatus 200.

Figure 3:
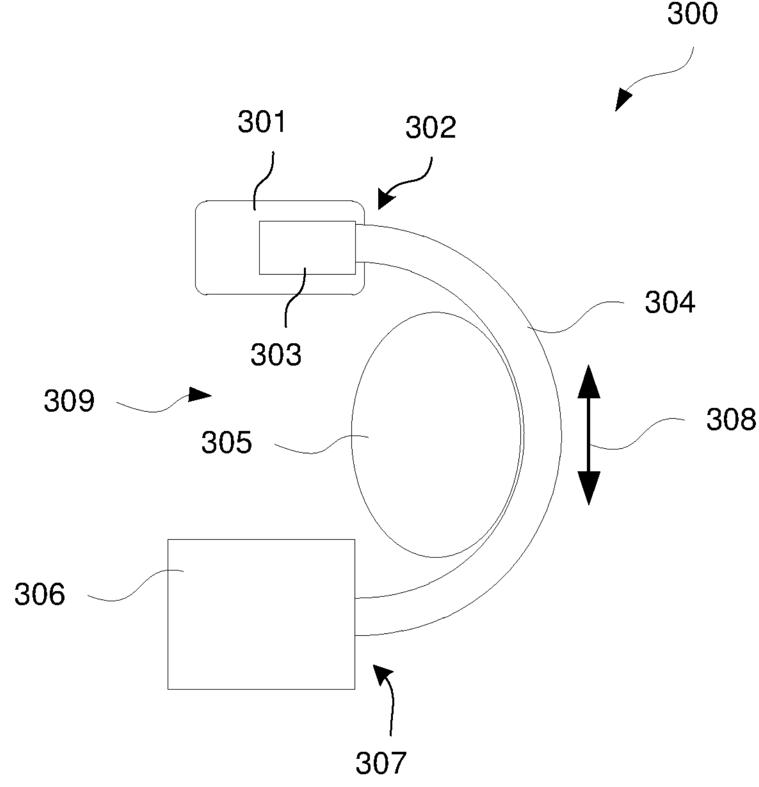
FIG. 3 is a component diagram illustrating alternative configurations for an automatic retention apparatus of the present disclosure.

Another aspect of the automatic retention apparatus of the present disclosure is illustrated at 300 in FIG. 3. A retention member 304 is shown that is separate and distinct from an object 305. Retention member 304 is optionally positionable around the object 305, and the retention member arranged 304 is optionally arranged and configured to engage the object to increase or decrease tension on the object. In this example, retention number 304 may be rigid, or semi-rigid and therefore may be movable in the direction of 308 depending on actuator 303. In this respect, retention member

304 may operate to apply tension by pulling toward the object 305, or alternatively by pushing toward the object 305.

In another aspect, retention member 304 may be optionally mounted to an anchoring object 306 at, or adjacent to, a first end 307. A second end 302 may engage actuator 303 within a housing 301 of the automatic retention apparatus. In this example, retention member 304 may be configured to apply tension to an object 305 where one end of the retention member 304 is acted on by an actuator 303, and the other end is mounted to an anchor that is separate from the housing 301.

In another aspect, the retention member 309, anchoring object 306, and the housing 301 together define an opening 309 within which object 305 may be positioned. For example, object 305 may be positioned such that retention member 304 is substantially perpendicular to the portion of object 305 that is positioned within the opening 309.

Figure 5:
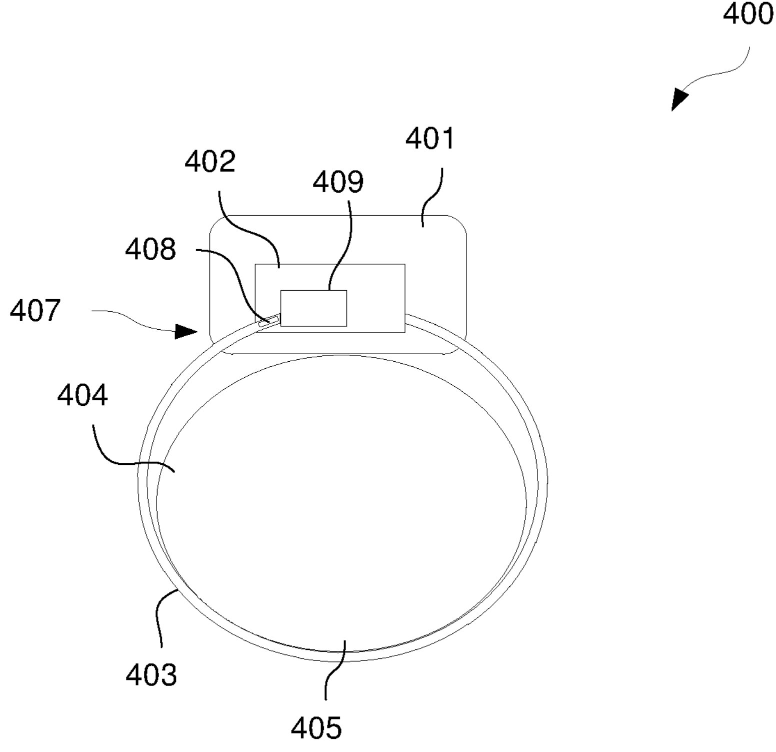
FIG. 5 is a component diagram illustrating additional aspects of the features illustrated in FIG. 4.
Figure 6:
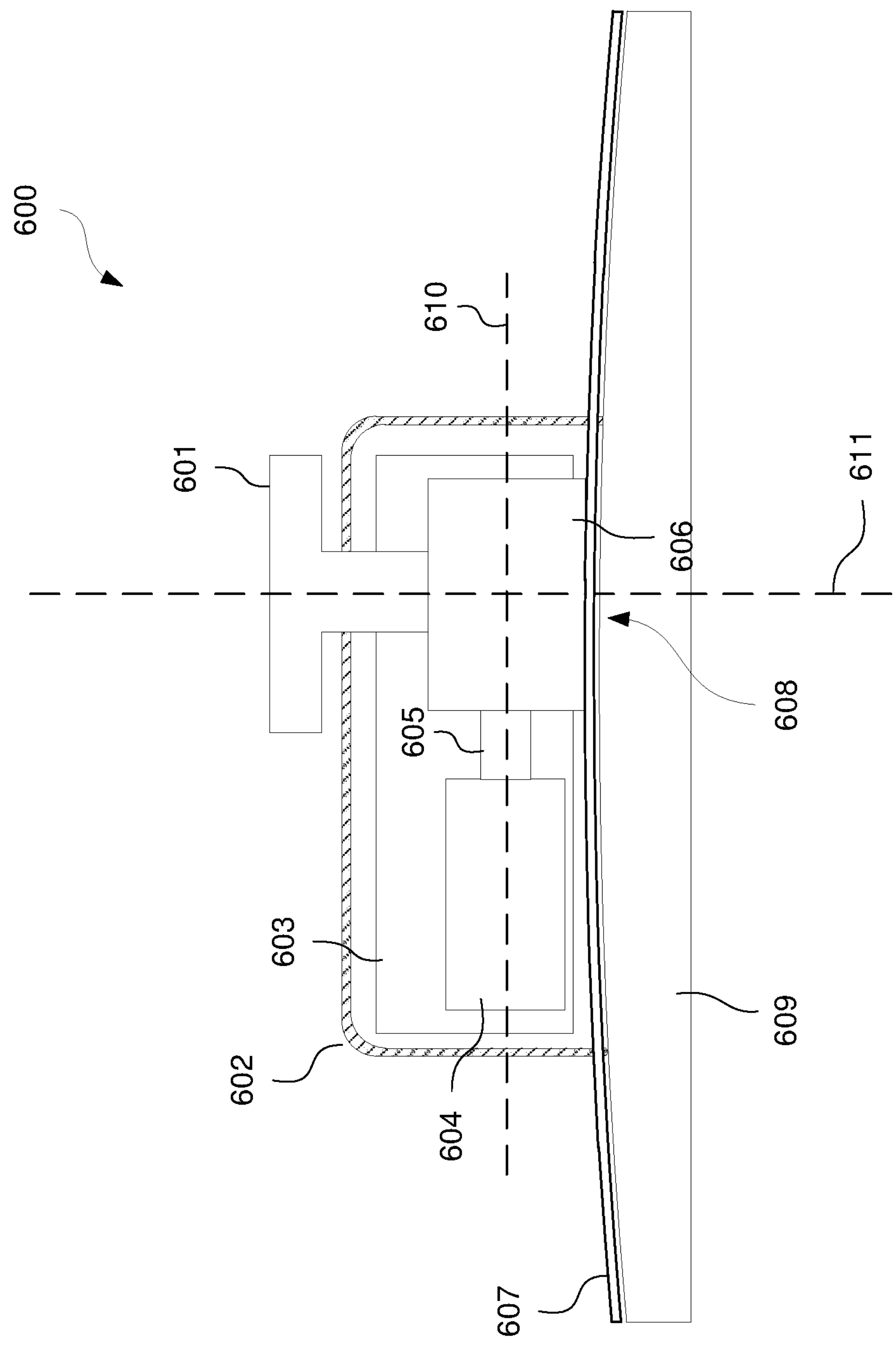
FIG. 6 is a component diagram illustrating alternative configurations for an automatic retention apparatus of the present disclosure.

FIGS. 5, and 6 illustrate another example of an automatic retention apparatus 400 of the present disclosure that includes a retention member 403 that includes a flexible substrate 404. In one example, the flexible metallic substrate is a metallic bi-stable spring. In another example, the retention member 403 is optionally constructed primarily of bi-stable metallic material such as a bi-stable metallic spring.

Figure 4:
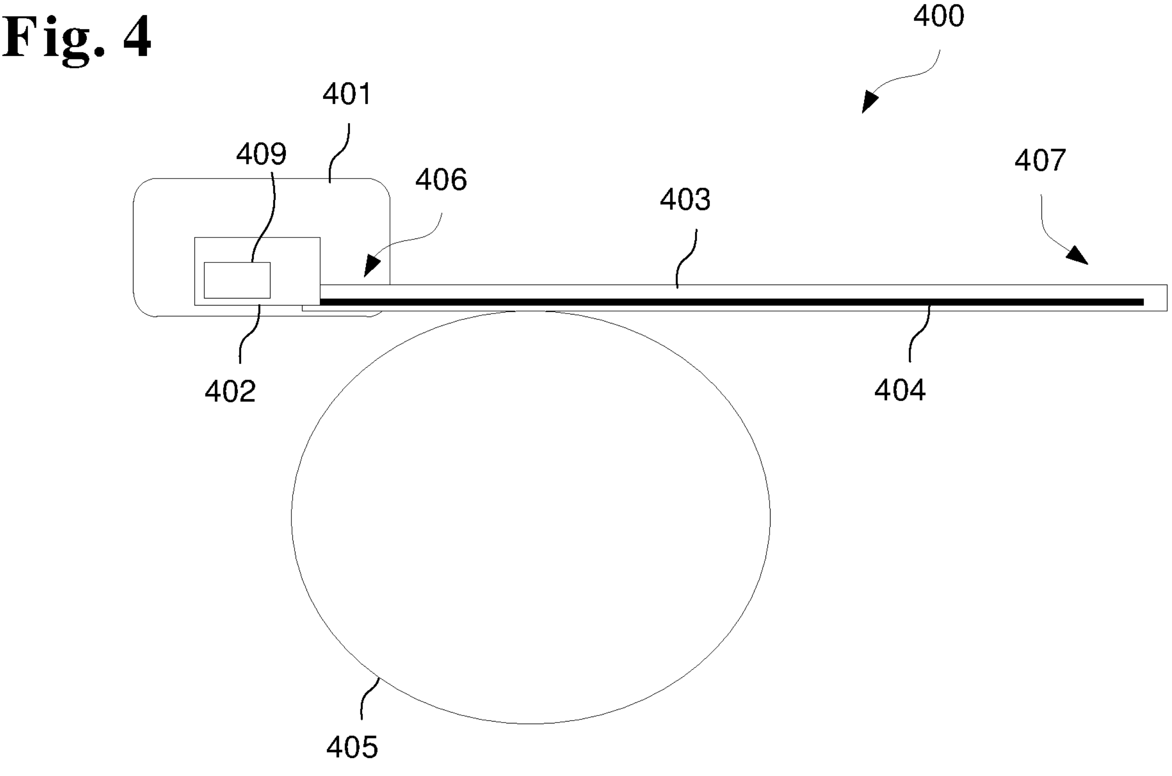
FIG. 4 is a component diagram illustrating alternative configurations for an automatic retention apparatus of the present disclosure.

The flexible substrate 404 optionally has a flat state shown in FIG. 4, and a curled state shown in FIG. 5. The curled state of the flexible substrate shown in FIG. 5 is optionally suitable for conforming to an object 405. As shown in FIG. 4, the retention member 403 is in the flat state prior to application to object 405. The retention member 403 may be applied to object 405 by any suitable means, such as by pressing the retention member against the object 405 until the flexible substrate 404 curls about the object 405 as shown in FIG. 5.

In another example, the retention member 403 is operable to "snap" between the flat and curled states such that when curled, the retention member 403 forms a continuous loop around object 405. In another example, an anchor portion 406 of the retention member at, or adjacent to, a first end of the retention member, may be mounted to the housing 401. An engagement portion 407 of the retention member at, or adjacent to, a second end of the retention member 403 may be selectively engageable with an actuator 402 when the flexible substrate is in the curled state. The engagement portion 407 may include indexing elements 408 such as magnets, grooves, projecting hooks, or pins, and the like by which attachment portion 407 may be biased to automatically engage with corresponding gears, pins, magnets, or other elements of the actuator 402. In this way, the retention member may be easily applied to an object 405 by "slapping" the retention member 403 against the object 405 such that the retention member 403 automatically curls around the object 405 and the engagement portion 407 automatically engages the actuator 402.

In another aspect, the engagement portion 407 of the retention apparatus is optionally configured to automatically engage an optional rotating member 409 of the actuator when the retention member is in the curled state. In another aspect, the automatic retention apparatus 400 may include a control circuit as disclosed herein, and the control circuit may be configured to automatically activate the retention apparatus 401 when the retention member 403 is in the curled state. For example a sensor may be positioned to detect when the engagement portion 407 is adjacent the rotating member 409 and the control circuit may be responsive to this sensor and configured to automatically activate the rotating member 409 accordingly.

FIG. 6 illustrates at 600 additional aspects of the disclosed automatic retention apparatus and related concepts. A housing 602 separate and distinct from the object 609 is shown where the retention member 607 optionally passes through the housing 602, or optionally passes into an out of the housing through an opening defined by the housing. An actuator 603 is optionally mounted inside the housing 602, and optionally includes a rotating member 606 that may be positioned to engage the retention member 607 at an engagement region 608. In another aspect, the rotating member 606 optionally engages the retention member 607 inside the housing 602, such as in the case of where the retention member 607 passes into the housing through an opening. The retention member 607 may pass through one or more holes defined by the housing 602 to enter the housing from the sides, or in another example, in one or more holes defined on the bottom of the housing.

A motor 604 may be included and coupled to the rotating member by a connecting member 605 (e.g. a shaft, linkage, belt, chain or other suitable connecting member). In one example, the rotating member 606 may be rotatable around an axis of rotation 610 in a first direction to increase tension on the retention member 607, and in a second direction to decrease tension on the retention member. In another example, the rotating member 606 is optionally rotatable around an axis of rotation 611 in a first direction to increase tension on the retention member 607, and in a second direction to decrease tension on the retention member.

A manual control 601 is optionally included in the automatic tensioning apparatuses of the present disclosure for manually adjusting tension on the retention member 607. Rotating the manual control 601 results in rotation of the rotating member 606, thus allowing for an alternative means of adjusting the rotating member 606 where a motor 604 is absent, or where the motor 604 is malfunctioning.

Figure 7:
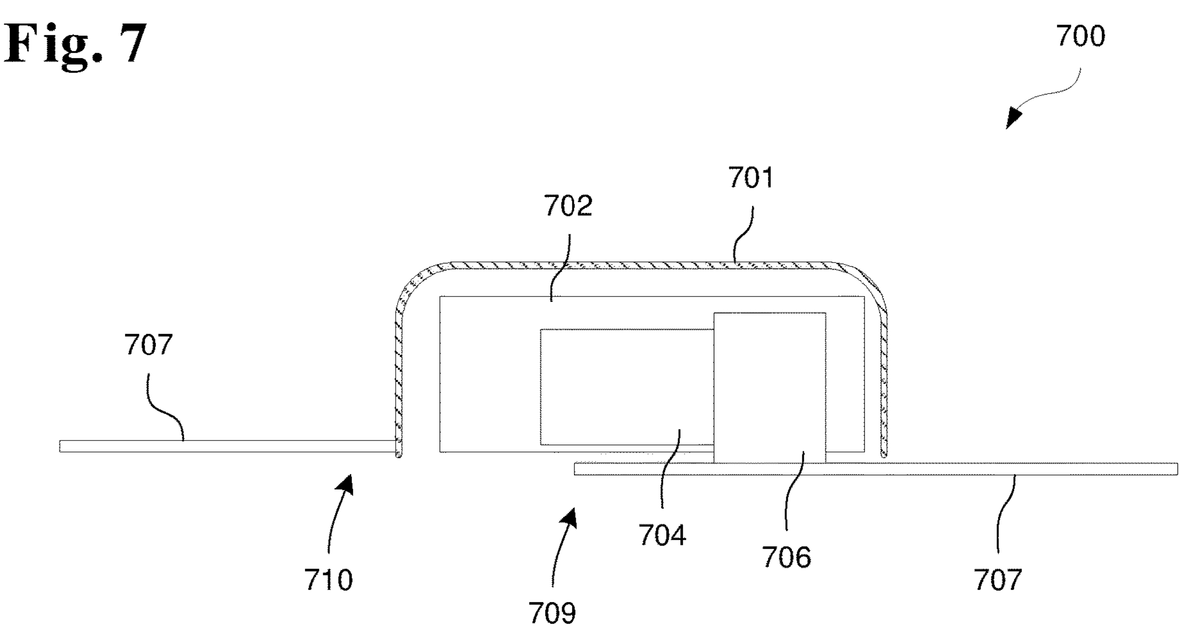
FIG. 7 is a component diagram illustrating alternative configurations for an automatic retention apparatus of the present disclosure.

Another example of the disclosed automatic retention apparatus is illustrated at 700 in FIG. 7. An actuator 702 may be optionally mounted in a housing 702, and the actuator may include a motor 704 coupled to a rotating member such as a rotating member 706. The rotating member 706 may be coupled to motor 704 by any suitable arrangement of devices for transferring torque from the motor 704 to the rotating member 706 such as by shafts, linkages, belts, chains, gears, and the like. In this example, the rotating member 706 extends out of the housing to engage the retention member 707 at an engagement region 708 that is at, or adjacent to, a first end 709 of the retention member. A second end 710 is optionally mounted to the housing. In another aspect, housing 701 and the second end 710 may optionally be fused together, or formed as a single unitary structure.

Figure 8:
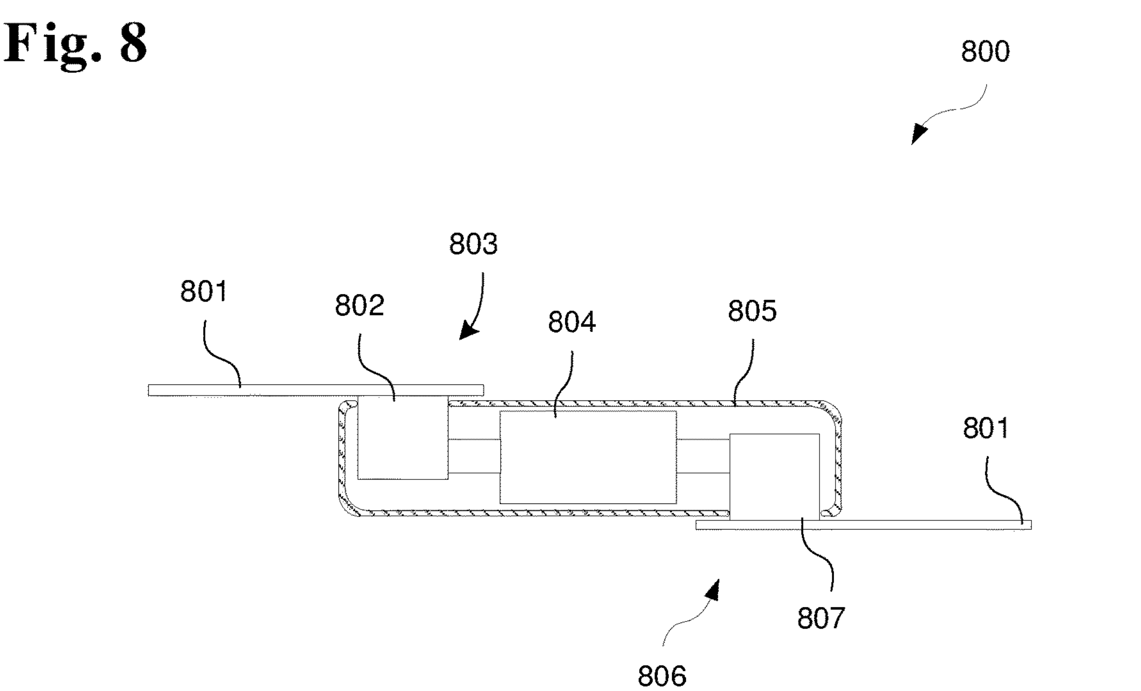
FIG. 8 is a component diagram illustrating alternative configurations for an automatic retention apparatus of the present disclosure.

In another example of the disclosed auto-tensioner concept illustrated at 800 in FIG. 8, a retention member 801 optionally includes a first end engagement region 803 coupled to a first rotating member 802, and a second end engagement region 807 optionally coupled to a second rotating member 807. In this example, the rotating members 802 and 807 are optionally coupled to a drive system 804, which may include a single motor coupled to both rotating members 802 and 807, or multiple motors working in concert, each coupled to a different rotating member. Either rotating member 802 or 807, or both, may extend out of housing 805 on opposite sides of the housing as shown, or on the same side. In this example, either end of the retention member 801 may be engaged and acted on to increase or decrease tension without being mounted to housing 805.

Figure 9:
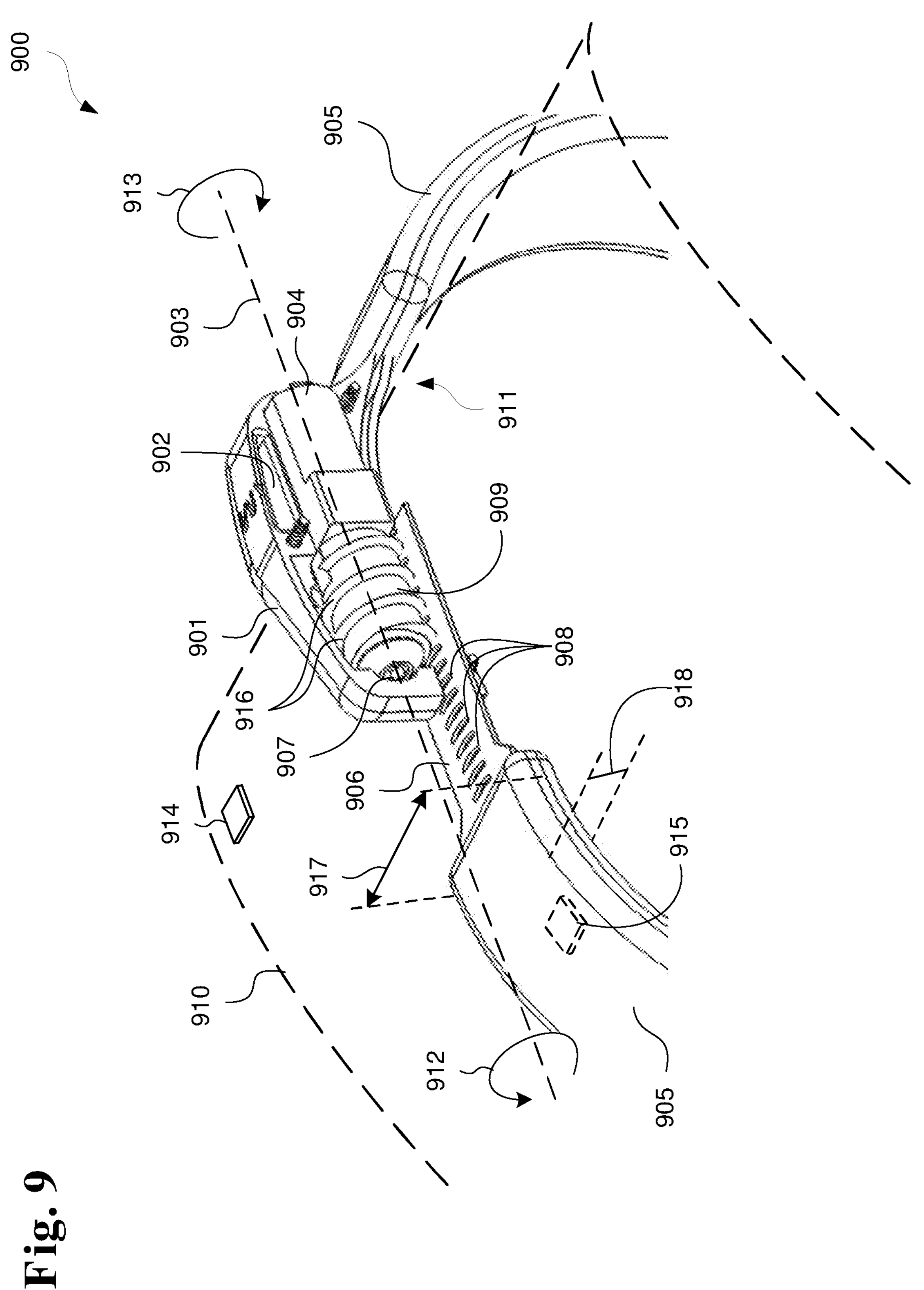
FIG. 9 is a cutaway perspective view of an automatic retention apparatus of the present disclosure.

FIG. 9 illustrates other aspects which may be incorporated in the disclosed examples of an automatic retention apparatus. An exemplary automatic retention apparatus 900 is shown for automatically adjusting tension on an object 910. A retention member 905 may be included that is optionally separate and distinct from object 910, and may be positioned around the object. The retention member 905 may be arranged and configured to engage the object 910 to increase or decrease tension on the object according to the present disclosure.

The retention apparatus 900 may include a housing 901 separate and distinct from the object 910, and the retention member 905 may be mounted to the housing by any suitable means, one example of which is shown at 911 where the retention member is bonded to the housing. Any suitable bonding technique may be employed such as by fasteners, adhesives, solvents, ultrasonic welding, or chemical bonding to name a few nonlimiting examples. In another aspect, the mounting at 911 may be achieved by forming the housing 901 and the retention member 905, or a portion thereof, as a single unitary structure.

An actuator may be mounted inside the housing 901 that optionally includes a motor 904 coupled to a rotating member 909 that optionally rotates on a shaft 907. The rotating member 909 may be positioned to engage the retention member 905. In this example, the rotating member includes a worm gear that optionally extends out of the housing 901 toward the object 910 to engage an engagement portion 906 of the retention member 905 adjacent to the housing. Engagement portion 906 includes one or more grooves or openings 908 defined by the engagement portion 906. Grooves 908 engage one or more teeth 916 of the rotating member 909. The rotating member 909 is optionally rotatable around an axis of rotation 903 that may be substantially parallel to the retention member 905 wrapped around the object 910.

In another aspect, using a worm gear for the rotating member 909, or for other examples of a rotating member of the present disclosure, where the teeth of the gear engage grooves like grooves 908, may advantageously provide a braking mechanism without additional wear or power usage. Using a worm gear may reduce or eliminate the opportunity for the rotating member to spin backwards thus unintentionally releasing tension on the engagement portion 906 and the retention member 905 in general.

The rotating member 909 may be rotated by a motor 904 controlled by a control circuit 902 of the present disclosure. The rotating member 909 may rotate in a first direction 912 to increase tension on the retention member 905, and in a second different direction 913 to decrease tension on the retention member.

The automatic retention apparatus may include at least one sensor 914 and/or 915 of the present disclosure which may be arranged and configured to sense changes in a sense parameter associated with the object 910. Control circuit 902 may be included that is optionally responsive to input from the sensor(s) 914 and 915. The control circuit 902 may be configured to control the actuator according to the input from the sensors as disclosed herein, the control circuit being configured to control the motor 904 to actuate the rotating member 909 to rotate it in the first or second direction 912 and 913 respectively to adjust tension on the retention member based on input from the sensor The sense parameters sensed by sensors 914 and 915 may be any parameters of interest in determining when, and to what extent, the tension on retention member 905 should be adjusted. In the case where the object 910 is a human or animal appendage, example sense parameters include, but are not limited to, body temperature, heart rate, nearby blood flow rate, nearby blood pressure, blood oxygen, perspiration, respiration rate, or electrical or chemical impulses related to heart beat, stress, emotion, pain, and the like.

In another aspect, sensor 914 may be mounted to object 910 separate from the housing 901, and may be configured to establish and maintain a communication link between sensor 914 and control circuit 902. In another aspect, sensor 915 may be mounted to, or included as part of, retention member 905 and may obtain sensor input from object 910 by virtue of close proximity of the retention member 905 to the object 910.

In another aspect, the retention member 905 illustrated in FIG. 9 is optionally substantially rigid and relatively inflexible. The retention member 905 may also define a width 917 and a thickness 918, and in some examples, the retention member may be wider than it is thick. That is to say, dimension 917 may be greater than dimension 918 allowing for retention member 905 to optionally be thin and flat relative to its length.

Figure 10:
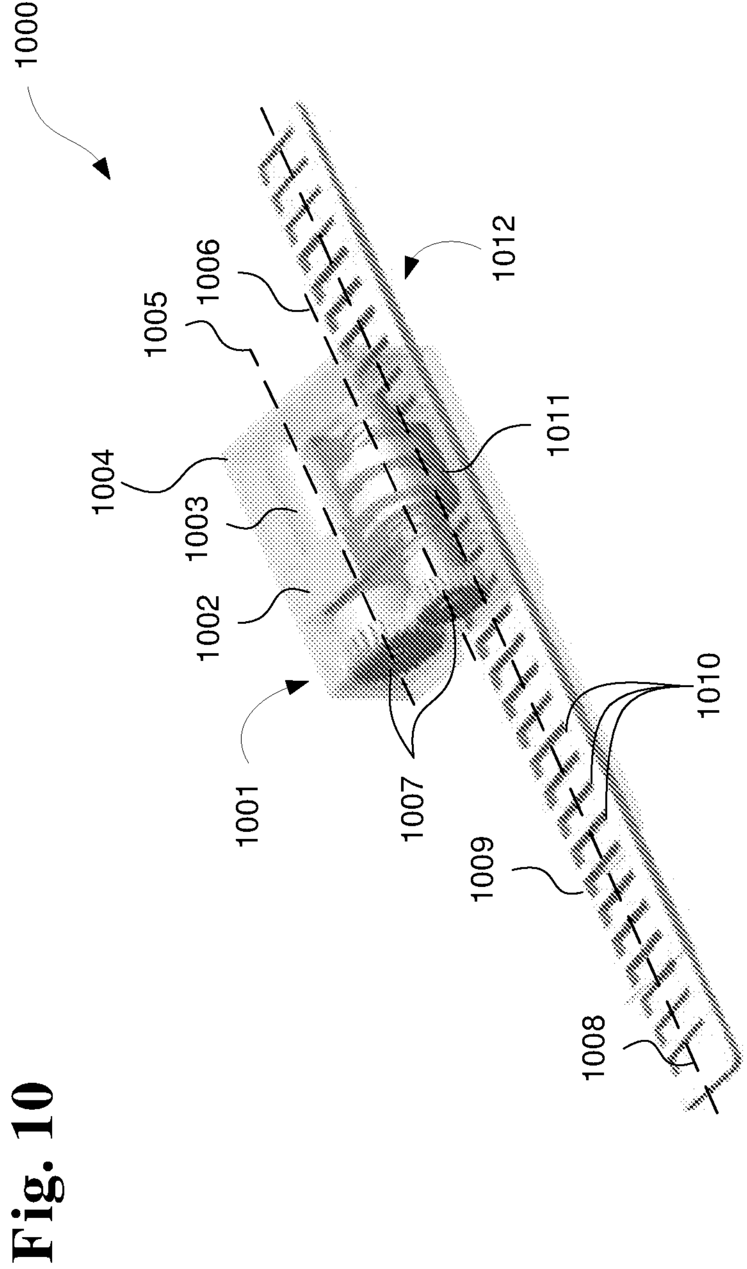
FIG. 10 is a partial cutaway perspective view of an automatic retention apparatus of the present disclosure.

In another example shown at 1000 in FIG. 10, an automatic retention apparatus of the present disclosure optionally includes a housing 1004 enclosing an actuator that is arranged and configured to rotate a drive gear 1011 to automatically increase or decrease the tension on a retention member 1009. The actuator mechanism of the present disclosure optionally includes a motor 1003 coupled to an optional reduction transmission at 1001. Transmission 1001 may include an optional reduction gearbox 1002. The reduction gear box may include one or more planetary or other gear sets for reducing the rotational speed of motor 1003, and/or for adjusting the resulting torque from motor 1003. In another aspect, the motor 1003 and/or transmission 1001 may define a motor axis of rotation 1005. Axis 1005 may be defined by one or more shafts or gears of motor 1003 and/or reduction gear box 1002.

Transmission 1001 may also include one or more transfer gears 1007 which may, or may not, further change the gear ratio between motor 1004 and drive gear 1011. Drive gear 1011 is optionally rotating on a separate drive gear axis of rotation 1006 which may be separate or offset from, but optionally parallel to, motor axis of rotation 1005.

Drive gear 1011 may be mounted within housing 1004 adjacent to retention member 1009. Retention member 1009 may define an engagement portion 1012 that optionally includes multiple grooves, holes, or openings 1010 that may be engaged by drive gear 1011. In another aspect, some or all of these openings 1010 may be through holes passing through retention member 1009 from an opening on one side to an opening on the opposite side of retention member 1009. In another aspect, retention member 1009 defines a longitudinal axis 1008 extending along the retention member in a direction generally perpendicular to the object retention member 1009 may be wrapped around.

Figure 11:
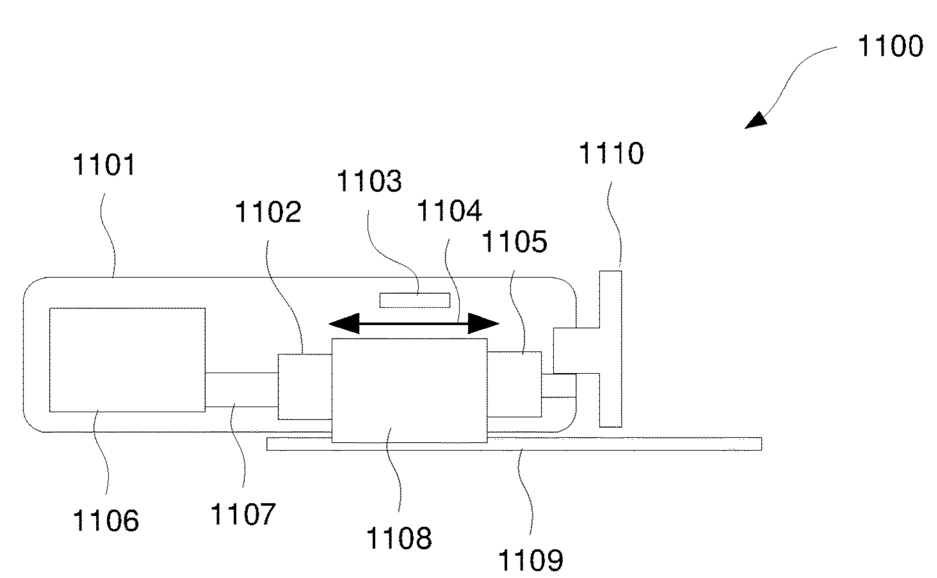
FIG. 11 is a component diagram illustrating alternative configurations for an automatic retention apparatus of the present disclosure.

In another example illustrated in FIG. 11, an automatic retention apparatus 1100 according to the present disclosure optionally includes and actuator 1101 of the present disclosure arranged and configured to engage a retention member 1109. The actuator 1101 optionally includes a motor 1106 coupled to a rotating member 1108 such as a worm gear, or other rotating member as disclosed herein. The rotating member 1108 may be mounted on a shaft 1107, or other suitable mechanical device for transmitting torque from the motor 1106 to the rotating member. The rotating member

1108 may be mechanically coupled to an optional manual tension control 1110 which may be useful to manually adjust the tension of the retention member 1109 by applying torque to the rotating member 1108 in response to input from a user. Manual tension control 1110 may be mechanically coupled to shaft 1107, or directly to rotating member 1108.

The automatic retention apparatus may include a biasing element 1102 positioned adjacent to the rotating member 1108, and optionally a second biasing member 1105. The biasing elements 1102 and/or 1105 may be arranged and configured to bias the rotating member 1108 in a direction opposite the tension in the retention member. A sensor 1103 may be positioned within the housing of the apparatus 1100 to register transverse movement 1104 of the rotating member 1108 as it repositions along the shaft 1107. This movement may be used to determine the level of tension the retention member is currently experiencing.

In another aspect, the biasing members 1102 and/or 1105 may be operable to automatically adjust tension on retention member 1109. For example, where the motor 1106 is absent, or is inoperable, the optional manual tension control 1110 may be activated to apply tension to retention member 1109. The biasing elements 1102 and 1105 may thus automatically adjust resulting tension as the rotating member 1108 moves laterally as shown at 1104. In another aspect, where the motor 1106 is operable and is operable to rotate the rotating member 1108, the biasing elements 1102 and/or 1105 may automatically adjust tension on retention member 1109 to dampen momentary increases or decreases in tension as the motor 1106 is adjusting tension on the retention member, or after the motor 1106 has stopped turning and the tension has been set, but the object experiences forces acting on it, or from within the object itself, which cause a momentary increase or decrease in tension applied by the automatic retention apparatus.

Figure 12:
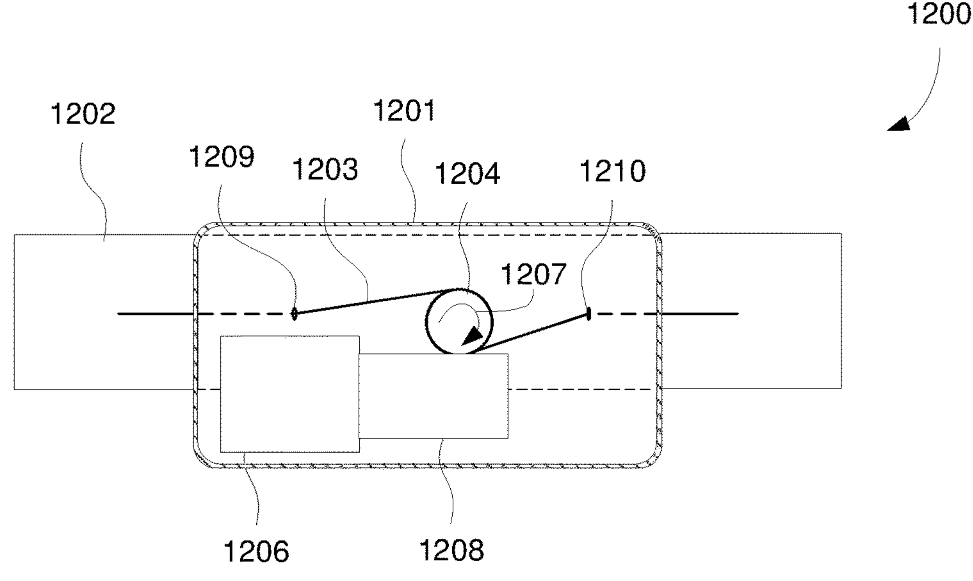
FIG. 12 is a component diagram illustrating alternative configurations for an automatic retention apparatus of the present disclosure.

In another aspect, the automatic retention apparatuses of the present disclosure may include a winding mechanism for engaging a retention member. An example of this concept is illustrated in FIG. 12 where an automatic retention apparatus 1200 is illustrated having a housing 1201 and an engagement portion 1203 of a retention member 1202. The engagement portion 1203 winds and unwinds around a rotating member 1204 inside the housing. The rotating member 1204 may include a shaft mechanically engaging with an optional gear mechanism 1208 driven by a motor 1206. Tension may be applied to the retention member 1202 when the rotating member 1204 is rotated in a first direction 1207 thus winding the engagement portion 1203 of the retention member onto rotating member 1204. Engagement portion 1203 may be a single piece of cable, wire, or any other suitable material, or may comprise multiple pieces such as a separate pieces coupled to rotating member 1204 and extending outwardly to engage retention member 1202. In another aspect, engagement portion 1203 may enter the housing 1201 at an opening 1209 and/or 1210 which may be in a side of the housing 1201 facing the retention member 1202, or on in any other suitable location.

In another aspect, the gear mechanism 1208 may include a worm gear with teeth engaging teeth of the rotating member 1204. Such a configuration may advantageously provide a braking mechanism to reduce or eliminate the opportunity for the rotating member to spin backwards and unintentionally release tension on the engagement portion 1203. In another aspect, the retention member 1202, and/or the engagement portion 1203 may include elastic elements such as elastic bands, springs, rubber bands, or other similar biasing elements to automatically unwind engagement portion 1203 from rotating member 1204 when the rotating member is actuated to reduce tension.

Figure 13:
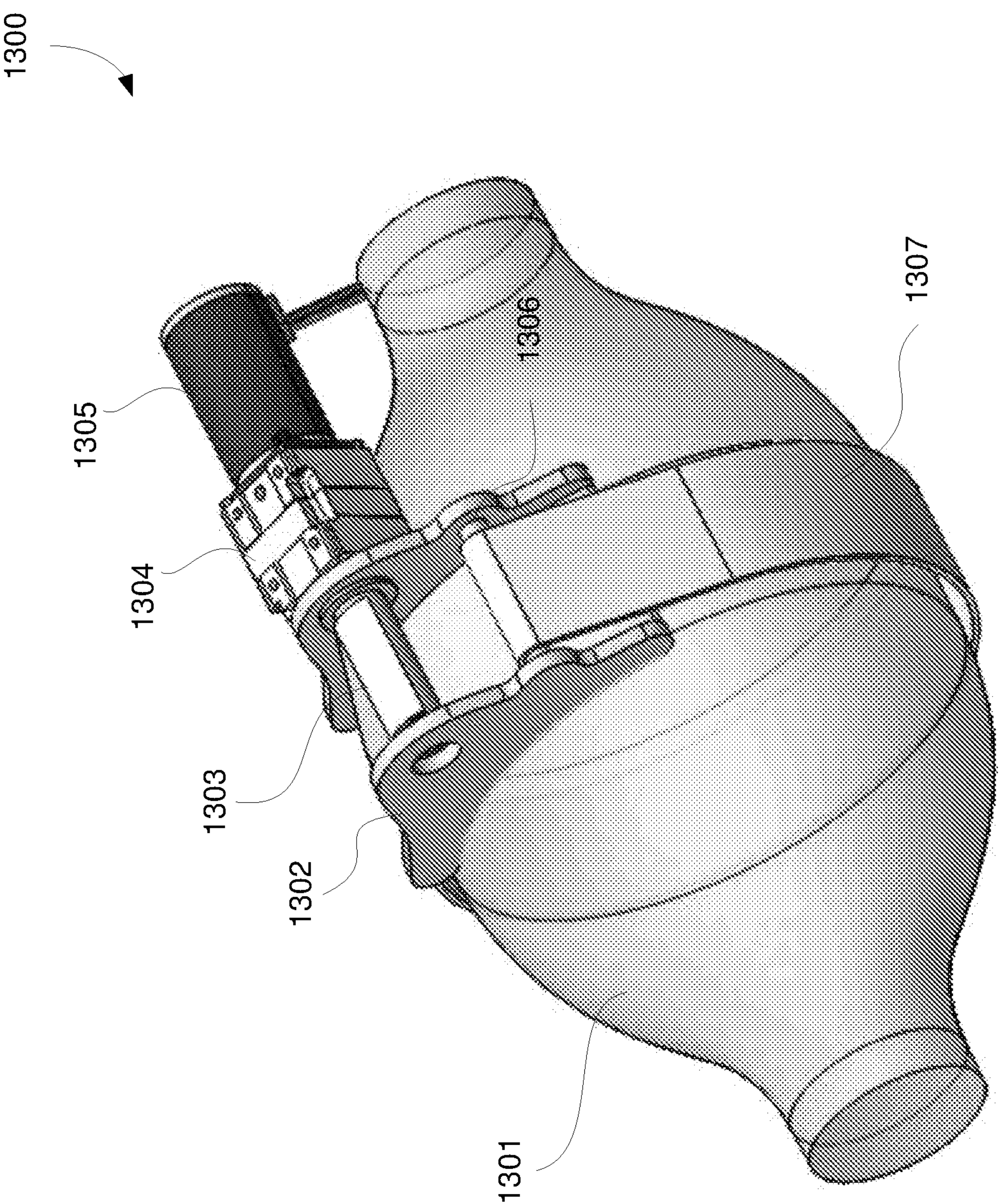
FIG. 13 is a perspective view of an automatic retention apparatus of the present disclosure.

In another example, shown in FIG. 13, an automatic retention apparatus 1300 is illustrated having an optional motor 1305 coupled to an optional drive mechanism 1304. The apparatus 1300 may include a rotating member 1303 for applying tension to a tension member 1307. A frame 1302 may be included for mounting the rotating member in alignment with the motor 1305 and drive mechanism 1304. An anchor pin 1306 is optionally provided for anchoring one end of the retention member 1307 so that when rotating member 1303 is actuated by the drive mechanism 1304, tension is increased or decreased according to the direction of rotation. In one example, rotating member 1303 may be rotated multiple times to increase or decrease tension on the object 1301. In another example, the rotating member 1303 may be configured to rotating a single revolution, or a specific number of revolutions when the motor 1305 is activated. In another aspect, as mentioned herein elsewhere, the retention member 1307 may include rigid materials such as metal or polymeric materials, or retention member 1307 may alternatively include flexible or elastic materials such as rubber or fabric or other similar materials. In another aspect, object 1301 may be compressible and may define a first expanded shape when not under tension by the automatic retention apparatus 1300, and may define a second compressed shape when under tension by the automatic retention apparatus. In this way, the fluid, gas, or other contents of the object may be expelled in a controlled way according to actuation of the automatic retention apparatus.

Figure 14:
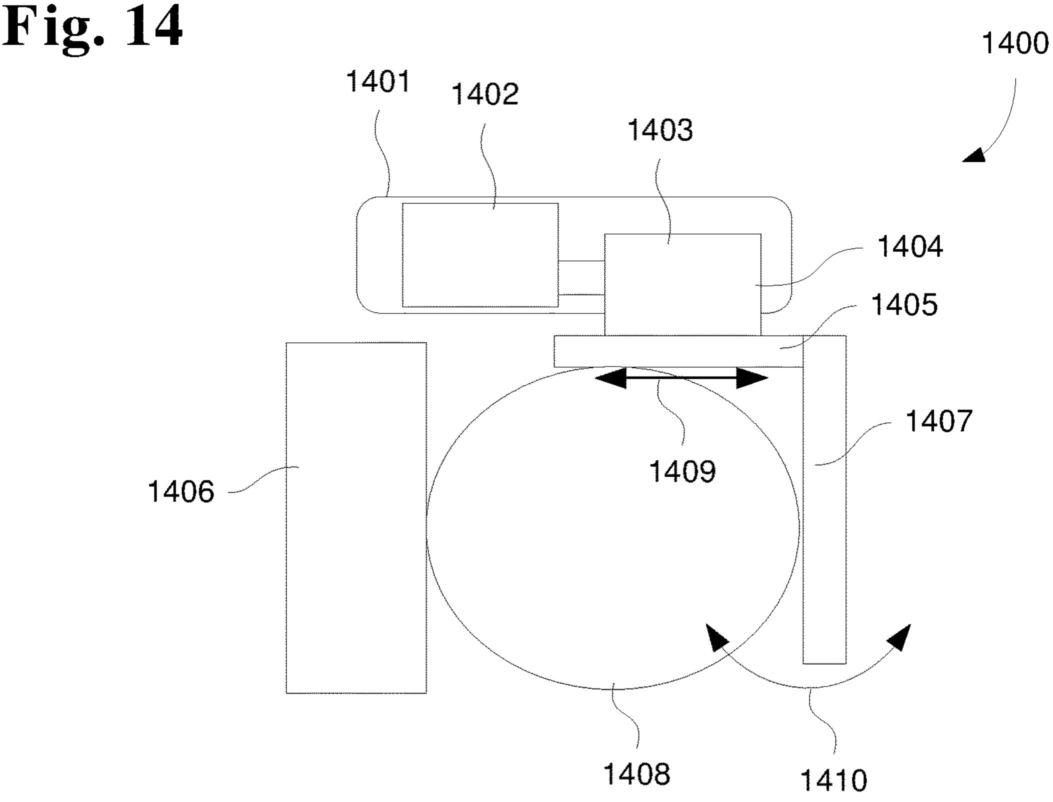
FIG. 14 is a component diagram illustrating alternative configurations for an automatic retention apparatus of the present disclosure.

In another aspect illustrated in FIG. 14, an automatic retention system 1400 according to the present disclosure may include an actuator 1401 with an optional motor 1402 coupled to a rotating member 1403. The rotating member 1403 may engage a retention member 1405 as disclosed herein to increase or decrease tension on the retention member and apply pressure to an object 1408.

Retention member 1405 may be coupled to an arm 1407 such that when the automatic retention system rotates rotating member 1403, tension may be applied to the retention member 1405 causing it to move arm 1407 closer to or further away from object 1408 as illustrated at 1409 thus increasing or decreasing the pressure applied to the object. In another aspect, applying tension to the retention member 1405 may cause arm 1407 to swing either toward the object 1408, or away from it as shown at 1410, thus selectively increasing or decreasing pressure on the object. In another aspect, the automatic retention system 1400 may be mounted adjacent to, or coupled to, an anchor or support object 1406. Thus movement of the arm 1407 towards or away from the anchor object 1406 may be initiated by actuation of the retention member 1405 to increase or decrease pressure applied to the object 1408.

Figure 15:
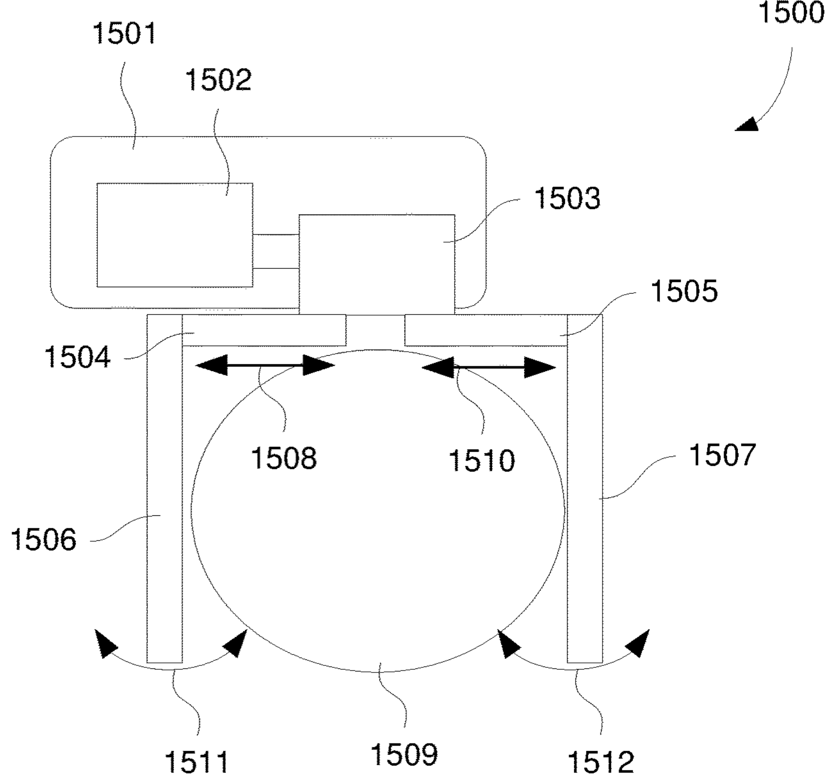
FIG. 15 is a component diagram illustrating alternative configurations for an automatic retention apparatus of the present disclosure.

In another aspect illustrated in FIG. 15, an automatic retention system 1500 according to the present disclosure may include more than one arm. In this example, the system includes an actuator 1501 with an optional motor 1502 coupled to a rotating member 1503. The rotating member 1503 may engage one or more retention members such as optional retention members 1504 and 1505 as disclosed herein to increase or decrease pressure applied to an object 1509.

Retention members 1504 and 1505 may be coupled to arms 1506 and 1507 respectively and arranged and configured so that when the automatic retention system rotates rotating member 1503, tension may be applied to the retention members causing them to move arms 1506 and 1507 closer to or further away from object 1509 as illustrated at 1508 and 1511 thus increasing or decreasing the pressure applied to the object. In another aspect, applying tension to the retention members 1504 and 1505 may cause arms 1506 and 1507 to swing either toward the object 1509, or away from it as shown at 1511 and 1512, thus selectively increasing or decreasing pressure on the object.

Figure 16:
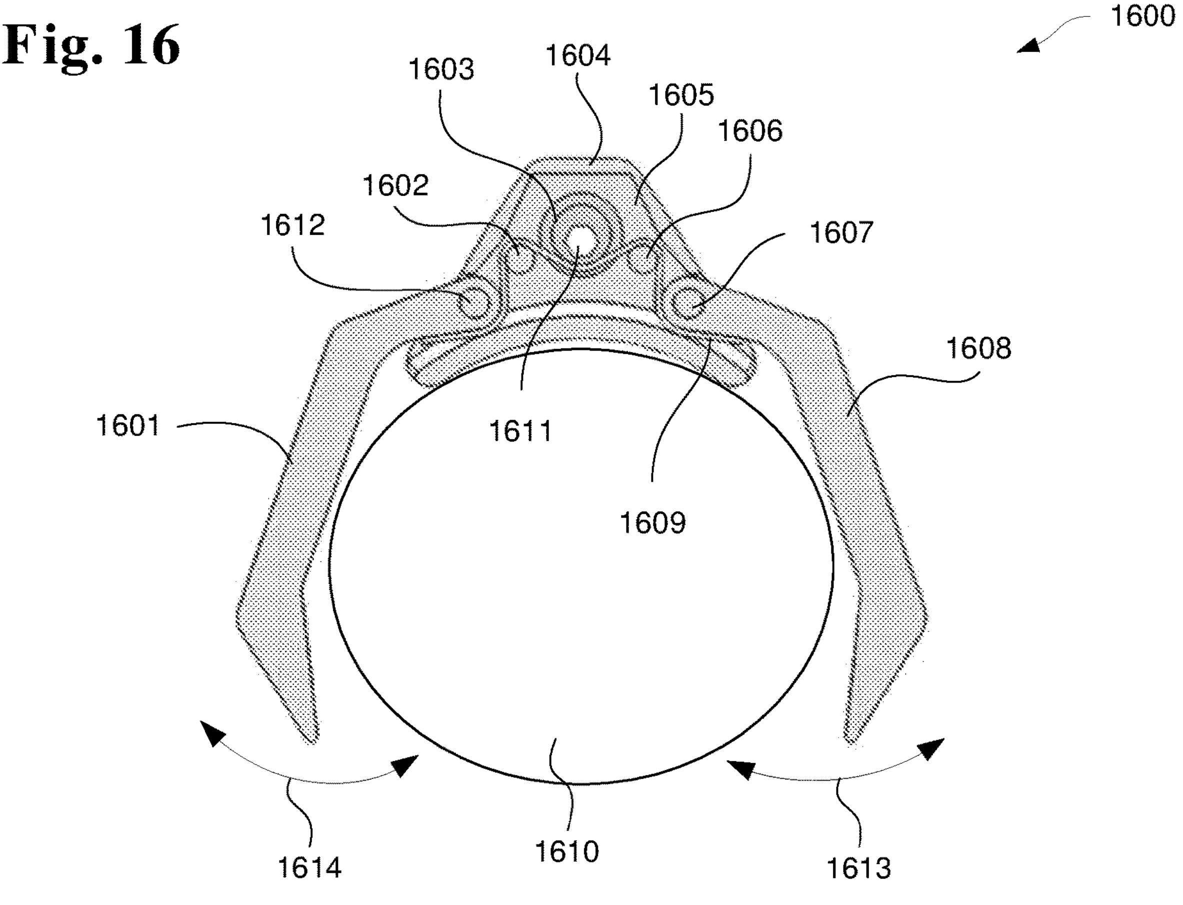
FIG. 16 is a cross sectional view of an automatic retention apparatus of the present disclosure.
Figure 17:
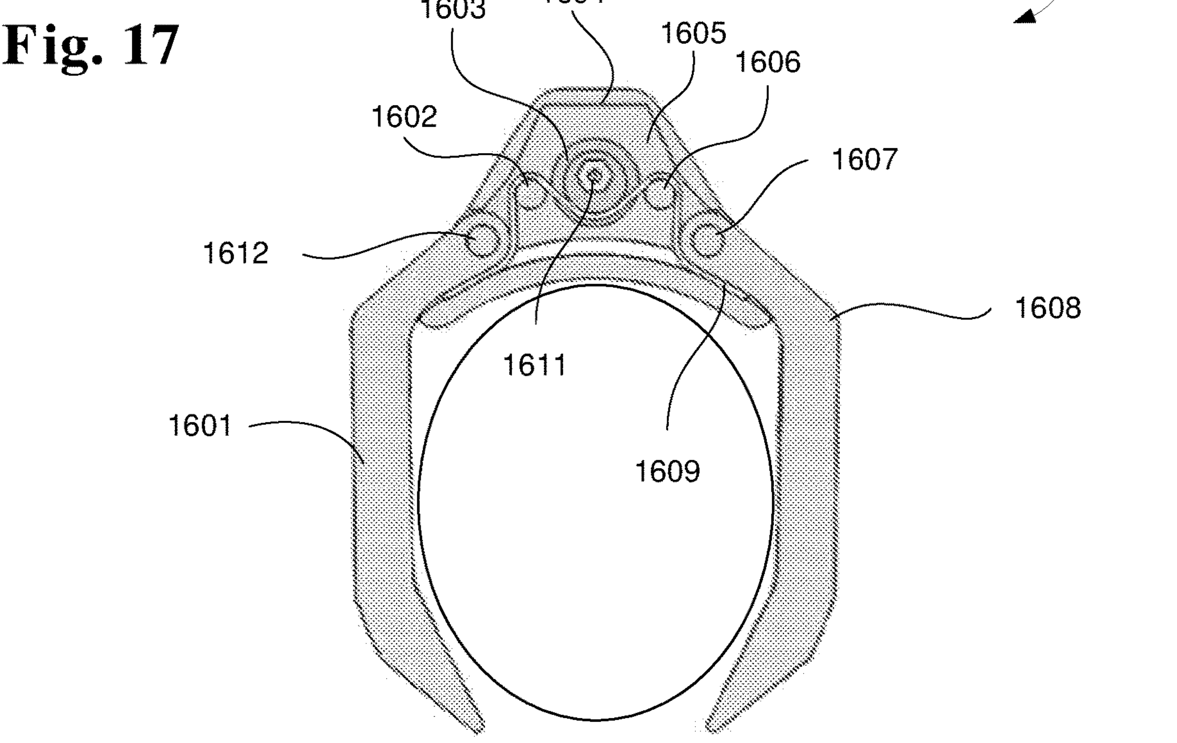
FIG. 17 is another cross sectional view of the automatic retention apparatus of FIG. 16.

In another aspect illustrated in FIG. 16 and FIG. 17, an automatic retention system 1600 is arranged and configured to adjust tension or compression on an object 1610 using two arms 1601 and 1608 that may be mounted to a frame 1605. Arm 1601 is optionally mounted at a mount point 1612 which provides for rotational motion of arm 1601 in the direction of 1614. Arm 1608 may also be mounted at a mount point 1607 which provides for rotational motion of arm 1608 in the direction of 1613.

A retention member 1609 like those discussed in the present disclosure engages a rotating member 1603. The retention member is coupled to the arms 1601 and 1608 adjacent to the mount points 1612 and 1607, and may also pass adjacent one or more pins or pulleys 1602 and 1606. Retention member 1609 is optionally coupled to the arms 1601 and 1608. For example, a first end of the retention member 1609 may be coupled to an arm 1601, and a second end opposite the first end of the retention member may be coupled to an arm 1608. The retention member 1609 may also engage rotating member 1603 such that rotation of rotating member 1603 causes tension to be applied to the retention member 1609 causing arms 1601 and 1608 to rotate inward toward the object 1610.

In one aspect, rotating member 1603 is optionally mounted as a rotating cam such that when in the "relaxed" position shown in FIG. 16, the retention member 1609 is also at a minimum tension state. When rotated by a motor, or other suitable means, the rotating member 1603 may press against the retention member 1609 as shown in FIG. 17 where the cam is at maximum displacement causing the maximum available tension on the retention member, and a corresponding maximum level of pressure against the object 1610. The disclosed control circuit may optionally control the rotation of the rotating member 1603 to interim positions between these two extremes depending on input from the available sensors.

Figures 18, 19:
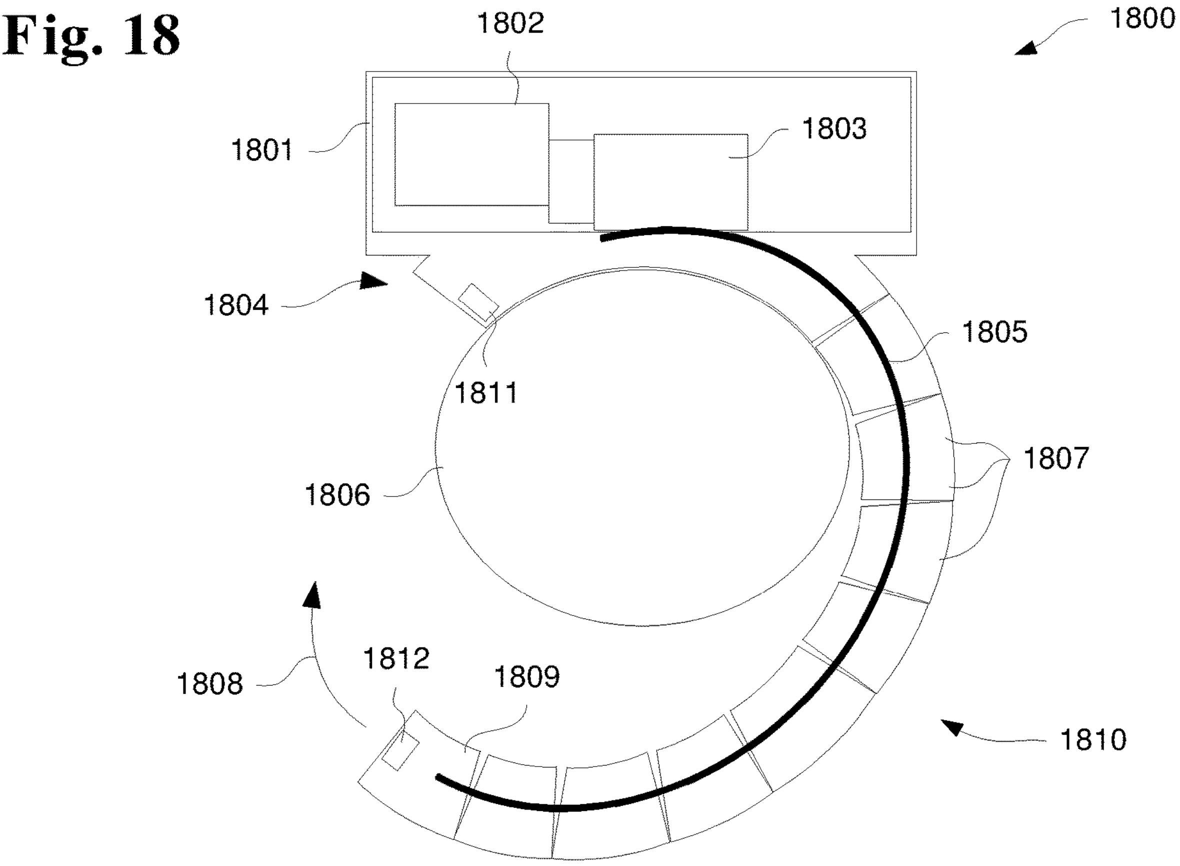
FIG. 18 is a component view of an automatic retention apparatus of the present disclosure.
FIG. 19 is another component view of the automatic retention apparatus of FIG. 18.

Illustrated in FIG. 18 and FIG. 19 is another example of the disclosed automatic retention system 1800 configured to adjust tension on an object 1806 using at least one arm shown in FIG. 18 in the relaxed state, and in FIG. 19 under tension. Automatic retention system 1800 includes multiple adjacent segments 1807 that are coupled together such by means of linkages, tension members, biasing elements, interlocking joints, or by any other suitable means. A retention member 1805 is coupled to the adjacent segments 1807 such that by applying tension to the retention member 1805, the adjacent segments tighten around the object 1806.

As discussed elsewhere in the present disclosure, an optional motor 1802 may be coupled to a rotating member 1803 that is arranged and configured to engage the retention member 1805. Rotating the rotating member 1803 in one direction optionally causes increased tension on the retention member, while retrograde rotation may result in reduced tension. As tension is applied, the arm segments 1807 tighten around the object 1806 causing the end segment 1809 to swing in the direction 1808 toward a frame portion 1804 of the housing 1801. The retention member 1805 is coupled to the arm 1810, and the arm is arranged and configured to rotate or otherwise move toward the object 1806 with increased tension on the retention member, and to rotate or move away from the object with decreased tension on the retention member 1805.

In another aspect, the arm 1810 optionally includes multiple interconnected segments 1807, and the retention member optionally passes through a channel defined by the segments and may be mounted to one of the multiple interconnected segments 1809 adjacent to the end of the arm. In another aspect the housing 1801 may operate as a mount for arm 1810 thus allowing the arm to squeeze and compress the object 1806 between the arm 1810 and the housing 1801. In another aspect, segments 1807 may be flexible or compressible to aid in providing tension to the object 1806 as the arm 1810 closes around the object, and optionally further compressing after arm 1810 is in place.

In another aspect, the engagement end segment 1809 of the retention apparatus is optionally configured to automatically engage frame portion 1804 when the arm 1810 is in the curled or closed state as shown in FIG. 19. In another aspect, the automatic retention apparatus 1800 may include a control circuit as disclosed herein, and the control circuit may be configured to automatically activate the retention apparatus 1800 when the arm 1810 is in the curled state. For example a sensor may be positioned to detect when the engagement arm is adjacent the frame portion 1804 and the control circuit may be responsive to this sensor and configured to automatically activate the rotating member 1803 accordingly.

The end segment 1809 may optionally include an alignment assembly 1812 coupled to or incorporated in the end segment 1809, and a corresponding alignment assembly 1811 coupled to or incorporated in frame portion 1804. As the arm 1810 wraps toward frame portion 1804, alignment assemblies 1811 and 1812 may be configured to automatically guide end segment 1809 toward frame portion 1804 so that when the end segment is adjacent to the frame, the end segment may also automatically latch or couple or otherwise connect with frame portion 1804 to optionally increase the tension that may be supplied by retention member 1805 and the arm 1810. Alignment assemblies 1811 and 1812 may include any magnets, hooks, clasps, slots, grooves, indexing members, or other members for aligning end segment 1809 with frame portion 1804, or any combination thereof.

Figure 20:
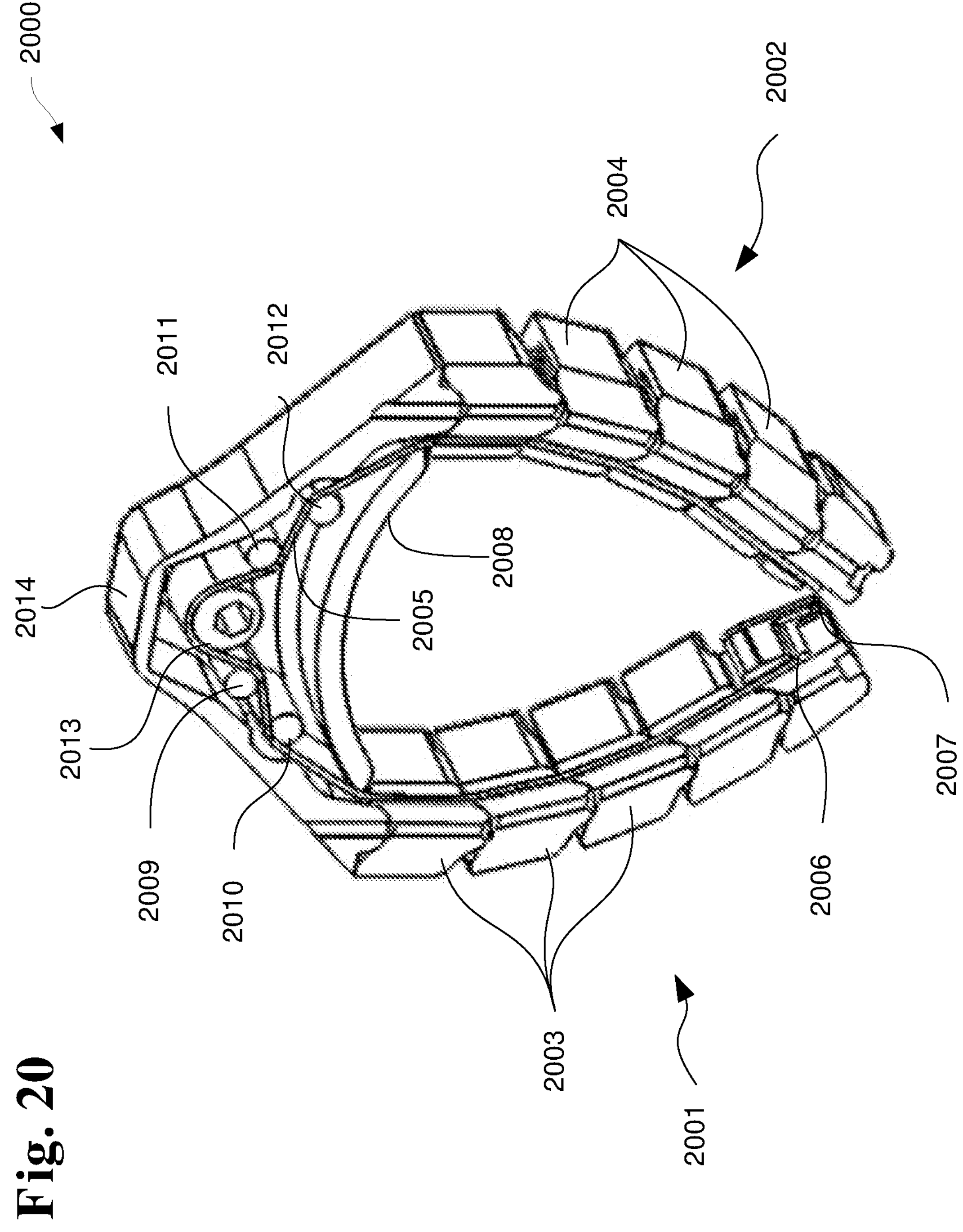
FIG. 20 is a cutaway perspective view of an automatic retention apparatus of the present disclosure.

Another example of a an automatic retention apparatus with one or more multi-segment arms is illustrated in FIG. 20. Arms 2001 and 2002 may include multiple individual segments 2003 and 2004 respectively. A retention member 2005 optionally passes through the individual arm segments, with one end of the retention member mounted at an end segment 2006 of arm 2001, and at an end segment 2007 of arm 2002.

A frame 2008 may be included to provide a mount for arms 2001 and 2002. The frame 2008 may also provide for pins, pulleys, bushings, bearings, or other aspects of the tensioning system. For example, frame 2008 may include pulleys or pins 2009-2012 which may be useful for redirecting or amplifying tension forces applied by retention member 2005 to the arms 2001 and 2002. Retention member 2005 may engage a rotating member 2013 within housing 2014 to increase or decrease the tension on the retention member 2005. Increasing tension on the retention member 2005 results in the arms rotating or swinging toward one another so as to compress an object held between them. In another aspect, the rotating member 2013 may operate as a cam where a portion of rotation, such as a half rotation, of the rotating member optionally places the retention member 2005 under maximum tension, and where a further portion of a rotation places the retention member under minimum tension. In another aspect, the rotating member 2013 may be configured to engage the retention member 2005 so that multiple rotations are required before maximum tension is achieved. This may be the case where the retention member 2005 winds onto rotating member 2013, or where rotating member 2013 includes a gear, or set of gears that are configured to engage the retention member 2005.

In another aspect, the individual segments of arms 2001 and 2002 optionally include corresponding projections and recesses, where the projection of one segment may be configured to easily rest within the recess defined by an adjacent arm segment to aid in aligning the segments. In another aspect, the individual arm segments may include interlocking portions or one or more biasing elements configured to keep the segments in proper alignment and adjacent to one another.

Figure 21:
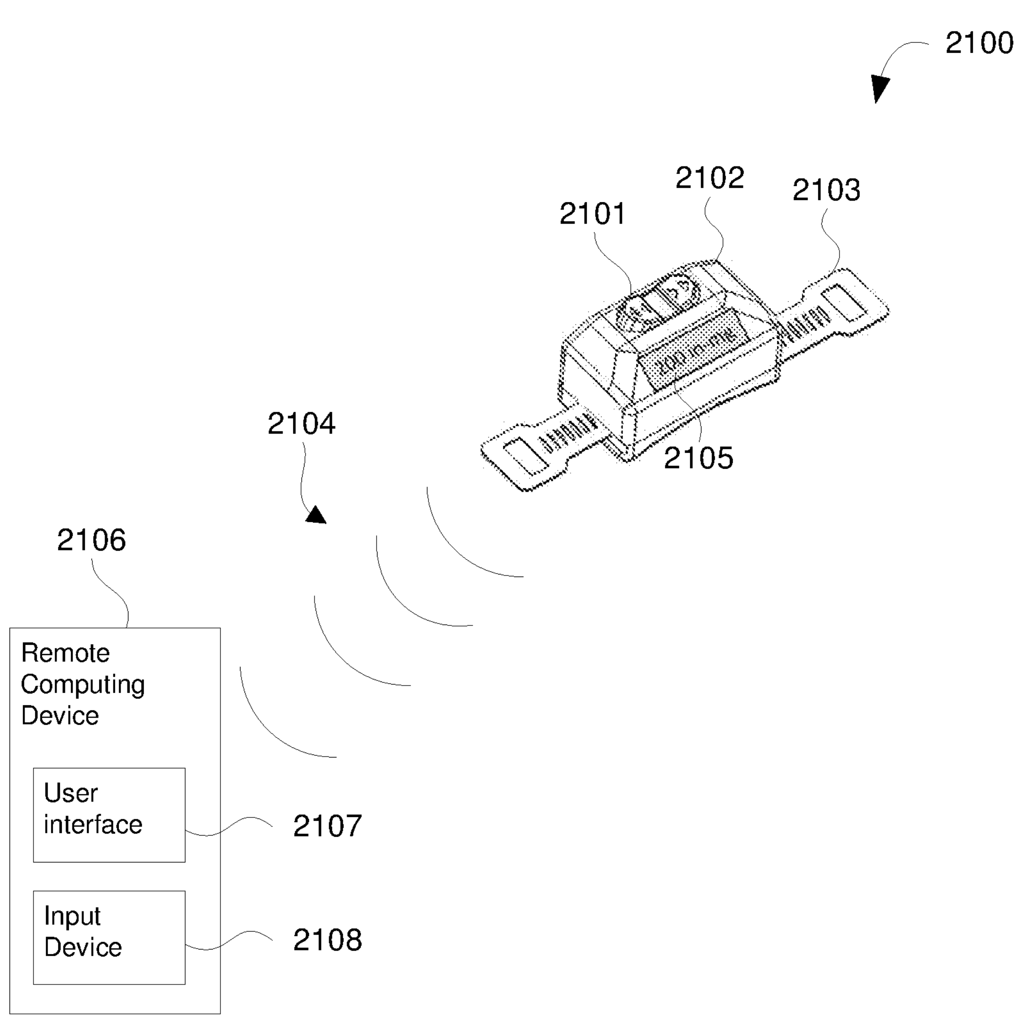
FIG. 21 is a component diagram illustrating alternative aspects of an automatic retention apparatus of the present disclosure.

Another example of the disclosed automatic retention apparatus is illustrated at 2100 in FIG. 21. The automatic retention apparatus 2100 includes a housing 2102 which contains the disclosed optional motors, rotating members, drive gears, and other components. A retention member 2103 extends away from the housing, which also includes optional user interface components which all a user to adjust one or more operational aspects of the automatic retention apparatus. For example, the automatic retention apparatus may include a display device 2105 mounted to the housing 2102. The display device 2105 may include one or more indicia providing information about functional aspects of the device such as the current tension thresholds, the current tension setting, whether the battery is charged, whether the device is malfunctioning, and the like. In another aspect, user interface components may include one or more buttons 2101 for adjusting operational characteristics of the device such as the tension on the retention member 2103.

Any suitable user interface may be used with the disclosed automatic retention apparatuses. In another example, a remote computing device such as a smart phone, tablet, laptop computer, desktop computer, server computer, or other computing device may include a user interface 2107 for display status or other operational aspects of the retention device, and one or more input devices 2108 for accepting input from a user adjusting the behavior of the automatic retention device. In on example, an app may be loaded onto a smart phone and used to adjust operational settings of the automatic retention device 2100. In another aspect, the remote computing device may communicate with the automatic retention apparatus 2100 by a communications link 2104, which may be a wired or wireless communications link. In another aspect, the same app executed by the remote computing device 2106 may be useful to control multiple automatic retention apparatuses.

Figures 22, 23:
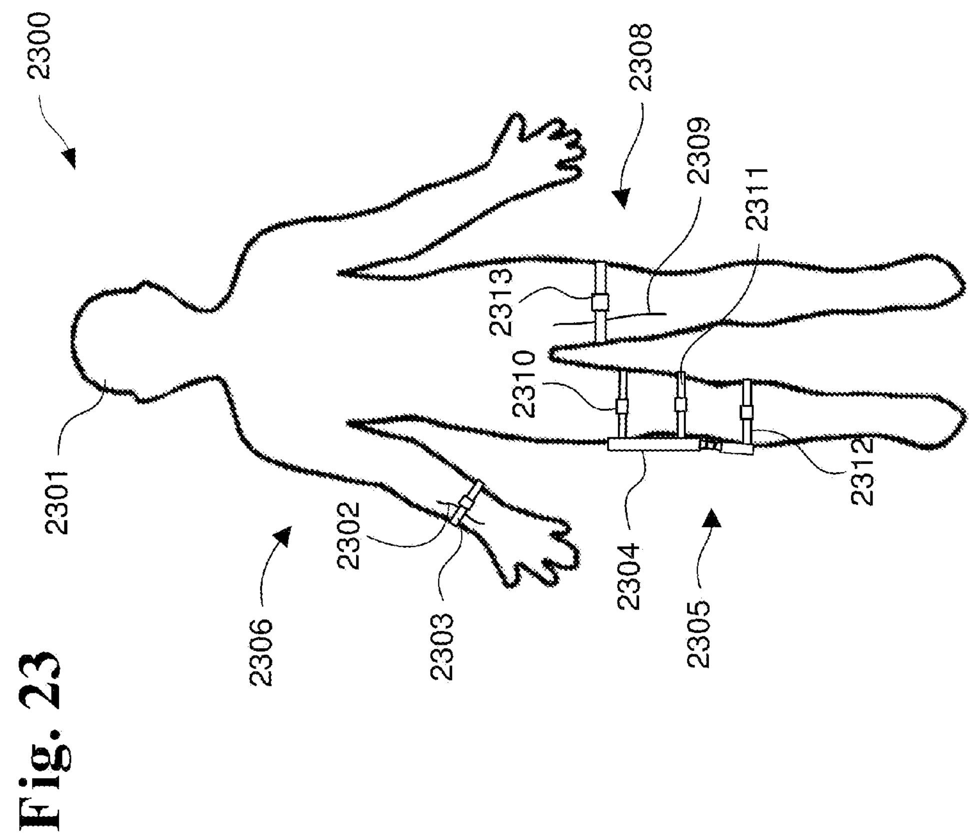
FIG. 22 is a perspective diagram illustrating aspects of an automatic retention system of the present disclosure.
FIG. 23 is component diagram illustrating examples of the positioning and usage of the disclosed automatic retention apparatus.

Another aspect of the disclosed automatic retention apparatus is illustrated at 2200 in FIG. 22. In this example, multiples of the disclosed automatic retention devices may be organized to operate as an automatic retention system for automatically adjusting tension on an object. In FIG. 22, automatic retention apparatuses 2202-2204 may be mounted to a frame 2201. The frame 2201 may be substantially rigid, and may include a joint region, such as in the case of a brace which may include a joint region 2205 to provide for the increased mobility of the user. At least one of the multiple automatic retention apparatuses (e.g. 2203) may be mounted on one side of the joint region 2205, and at least one other of the multiple automatic retention apparatuses (e.g. 2204) may be mounted on another side of the joint region. The joint region may include multiple rotating elements linked together to provide support and mobility for a human or animal user. The automatic retention system at 2200 may thus be useful as a brace or splint for a leg, knee, elbow, arm, back, or other location on a human or animal in need of additional support or protection.

Examples of the disclosed automatic retention apparatuses in use for a human or animal subject are illustrated in FIG. 23 at 2300. In one example an automatic retention apparatus 2303 may be positioned on a human or animal appendage such as arm 2306 or leg 2308 of a user 2301. Upon installation, the automatic retention apparatus may automatically determine from the disclosed sensors that are configured to detect aspects of the environment, or of the object, how much tension to apply to arm 2306 or leg 2308. For example, a radial artery 2302, or a femoral artery 2309 may have been injured due to accident, war, natural disaster, and the like, and an automatic retention apparatus 2303 or 2313 may be placed near the affected region to reduce or eliminate an otherwise life threatening loss of bodily fluids. As disclosed herein elsewhere, the automatic retention apparatus 2303 or 2313 may determine from sensing aspects of the object itself (e.g. reduced blood flow in the arm 2306 or leg 2308), or of the environment (e.g. ambient temperature, pressure changes, and the like) that tension should be applied immediately to reduce or eliminate the loss of blood from the radial artery 2302 or femoral artery 2309.

In another aspect, a user 2301 may have injuries in both the arm 2306 and the leg 2308, both of which may require immediate lifesaving care. The disclosed auto retention apparatuses may be quickly deployed as shown at 2300 and put to use at the same time, one on the arm, and one on the leg. This may allow a care giver to advantageously attend to other victims while the automatic retention apparatuses 2303 and 2313 automatically provide the necessary life-saving treatment. In the case of a mass-casualty incident where dozens of victims may be experiencing severe trauma, a single care-giver may thus be able to rapidly apply lifesaving care to multiple victims quickly by deploy multiple devices. In another aspect, the multiple devices for multiple victims may independently communicate data about each patient to one or more remote computing devices thus allowing a few care givers to deploy and monitor lifesaving care rapidly for many victims.

In another example, a knee brace 2304 may be installed at a knee 2305 of the user 2301 and may be configured to include an automatic retention system. The three automatic retention devices 2310-2312 used here as part of the automatic retention system of knee brace 2304 may automatically sense and apply the proper level of tension at each location along the user's leg so as to properly maintain the knee brace 2304 in position as the user moves. The disclosed apparatuses may be positioned in any useful location of a human or animal for the purpose of automatically applying pressure or tension.

In operation, the control circuit and/or other electronics in the various examples of an automatic retention apparatus disclosed herein is operable to automatically adjust the tension on the retention member. In one operational aspect, the control circuit is programmed to perform a power on process for the data collection and control electronics. The process may begin by receiving a power on command to activate the apparatus including the control circuit and any additional control electronics. The control circuit may initiate communication with an inertial sensor suite via a digital interface, and may also initialize a file system in the memory for recording data and maintaining configuration data such as the configuration data discussed herein. The control circuit may also begin calibration of all available sensors such as any inertial sensors. This may include configuring the resolution of the sensors and the sample rate. It may also include configuring sensor noise filter.

The control circuit may also be configured to execute a data collection and control algorithm. The algorithm may include retrieving the available stream of data from any available sensors representing the values of the various sense parameters generated by the sensors. The control circuit may apply/update a digital filter of state data, and/or use an adaptive algorithm such a neural network, or similar algorithm to identify important data features in the time and frequency domain of the incoming data stream. The control circuit may use the resulting data, configuration parameters, and real-time data features to calculate one or more values representing the tension to be applied to the retention member. The control circuit may compare the values to measured device parameters and communicate the tension values to the actuator to adjust the tension accordingly. The data collection and control algorithm may then repeat as necessary. The algorithm may execute multiple times a second such as more than 10 times a second, more than 1000 times a second, or more than a million times a second.

One example of circuit components for processing signal input and producing a motor control output is illustrated at 2400 in FIG. 24. These components may be used with, or included in components discussed herein elsewhere, particularly with respect to the components illustrated in FIG. 1 at 100. The control circuit at 2400 may include multiple sub circuits such as a sensor processing circuit 2414, a memory card interface 2434, and high-level control of decision logic circuit 2422, and external current watchdog circuit 2408, a low level Proportional Integral Derivative (PID) loop 2426, and the saturation compensation circuit 2428. External current watchdog circuit 2408 may include a hardware abort aspect which may operate as a current limiter to avoid overloading motor 2437. A motor current operational amplifier (or "Op Amp") 2402 passes signals representing the data value for motor current to a 14-bit Analog to Digital Converter (ADC) 2404. The sensor processing circuit 2414 may include any suitable sensors like sensors 115 that may include a 3-axis accelerometer 2412 and 3-axis gyro 2416 which may be used to estimate the motion state at 2418 by utilizing such filters as the FFT (Fast Fourier Transform), FIR (Finite Impulse Response), and IIR (Infinite Impulse Response). Memory card interface 2434 may include an SPI-bus and SD card reader 2436 with access to update configuration data 2435 which may include user configurable aspects or operating parameters of the automatic retention apparatus. The motion response executive 2420 then reads the motion state and configuration data and passes the result to high-level control decision logic 2422 which may then determine a target tension using target tension generation circuits 2424. This target tension may be compared to the actual tension calculated from motor current or sensor circuitry comparing aspects such as force, torque or position data. The result is passed to PID loop 2426 and saturation circuitry 2428 producing an output such as Pulse Width Modulation (PWM) output 2430 which may be provided to motor 2437 to automatically control tension on the retention member as discussed herein elsewhere.

Other disclosed concepts include the following numbered examples:

Example 1

An automatic retention apparatus for automatically adjusting tension on an object, comprising that includes a retention member that is separate and distinct from and positionable around the object, the retention member arranged and configured to engage the object to adjust tension or compression forces on the object.

Example 2

The automatic retention apparatus of any other example including a housing separate and distinct from the object, wherein the retention member is optionally mounted to the housing.

Example 3

The automatic retention apparatus of any other example including an actuator that includes a rotating member, wherein the rotating member is positioned to engage the retention member.

Example 4

The automatic retention apparatus of any other example wherein a rotating member is rotatable around an axis of rotation in a first direction to increase tension on the retention member and in a second direction to decrease tension on the retention member.

Example 5

The automatic retention apparatus of any other example including at least one sensor arranged and configured to sense changes in a sense parameter associated with the object.

Example 6

The automatic retention apparatus of any other example including a control circuit responsive to input from a sensor and configured to control an actuator according to the input from the sensor, wherein the control circuit is configured to control the actuator to rotate the rotating member in a first or second direction to adjust tension on the retention member based on input from the sensor.

Example 7

The automatic retention apparatus of any other example including a rotating member that optionally extends out of a housing to engage the retention member, and wherein the retention member is optionally adjacent to the housing, and/or the rotating member is optionally mounted inside the housing Example 8

The automatic retention apparatus of any other example including a rotating member that consists of, comprises, or includes a worm gear positioned adjacent to the retention member that is optionally arranged to engage holes, grooves, splines, pins, or through holes defined by the retention member.

Example 9

The automatic retention apparatus of any other example wherein the retention member is optionally rigid and wider than it is thick and optionally defines one or more holes engageable by the worm gear.

Example 10

The automatic retention apparatus of any other example wherein the retention member is optionally flexible or semi-rigid.

Example 11

The automatic retention apparatus of any other example wherein an engagement portion of the retention member engages a rotating member inside a housing, and wherein the housing is optionally fully or partially enclosed, and/or the housing optionally defines through holes through which the retention member may pass from outside the housing in order to engage the rotating member.

Example 12

The automatic retention apparatus of any other example that comprises a rotating member that includes a shaft, wherein an engagement portion of the retention member winds and unwinds around the shaft to increase or decrease tension on the object.

Example 13

The automatic retention apparatus of any other example wherein the retention member includes a flexible substrate having a flat state and a curled state, and wherein the curled state of the flexible substrate is optionally suitable for conforming to the object.

Example 14

The automatic retention apparatus of any other example wherein a first end of the retention member is mounted to a housing, and a second end of the retention member is selectively engageable with a rotating member when a flexible substrate of the retention member is in the curled state.

Example 15

The automatic retention apparatus of any other example wherein an engagement portion of the retention apparatus is configured to automatically engage a rotating member when the retention member is in a curled state.

Example 16

The automatic retention apparatus of any other example wherein a control circuit is configured to automatically activate the retention apparatus to begin applying tension to the retention member when the retention member is in to the curled state, or shortly after the retention member arrives in the curled state.

Example 17

The automatic retention apparatus of any other example wherein the retention member includes, or consists of, or is primarily made of a flexible substrate that is optionally a metallic or polymeric bi-stable spring.

Example 18

The automatic retention apparatus of any other example that includes a frame mounted to a housing, and optionally at least one arm rotatably mounted to the frame or the housing, wherein the retention member is optionally coupled to the at least one arm.

Example 20

The automatic retention apparatus of any other example wherein at least one arm is arranged and configured to rotate toward the object with increased tension on the retention member, and wherein the at least one arm is arranged and configured to rotate away from the object with decreased tension on the retention member.

Example 21

The automatic retention apparatus of any other example wherein at least one arm is arranged and configured to rotate toward the object with decreased tension on the retention member, and wherein the at least one arm is arranged and configured to rotate away from the object with increased tension on the retention member.

Example 22

The automatic retention apparatus of any other example that also includes at least one arm that has multiple interconnected segments, and wherein the retention member passes.

Example 23

The automatic retention apparatus of any other example that also includes at least one arm that has multiple interconnected segments, and wherein the retention member is mounted to one of the multiple interconnected segments adjacent an end of the arm.

Example 24

The automatic retention apparatus of any other example that also includes a biasing element positioned adjacent to a rotating member, wherein the biasing element is optionally arranged and configured to bias the rotating member in a direction opposite the tension in the retention member, and/or, the biasing element is optionally arranged and configured to bias the rotating member in the same direction as the tension in the retention member.

Example 25

The automatic retention apparatus of any other example that also includes biasing element that is, comprises, or is primarily made of a spring, and wherein the biasing element engages a rotating member while optionally sharing a common shaft with the rotating member.

Example 26

The automatic retention apparatus of any other example that includes at least two rotating members, a first and second rotating member, wherein the first rotating member is optionally positioned to engage the retention member at a first end, wherein the second rotating member is optionally positioned to engage the retention member at a second end, and wherein the first and second rotating members are separately or otherwise rotatable in a first direction to increase tension on the retention member and in a second direction to decrease tension on the retention member.

Example 27

The automatic retention apparatus of any other example wherein the object is a human or animal appendage, and wherein a sense parameter associated with a sensor of the retention apparatus includes any combination of blood pressure, body temperature, blood oxygen level, or heart rate.

Example 28

The automatic retention apparatus of any other example wherein a control circuit is configured to increase tension on the retention member when a sense parameter of a sensor matches a first target criteria, and wherein the control circuit is configured to decrease tension on the retention member when the sense parameter matches a second target criteria.

Example 29

The automatic retention apparatus of any other example that includes an environment sensor arranged and configured to sense changes in an environmental sense parameter associated with an environment surrounding the sensor, wherein a control circuit is responsive to the environmental sense parameter, and wherein the sense parameter comprises any combination of speed, angular momentum, velocity, movement, or acceleration.

Example 30

The automatic retention apparatus of any other example wherein an environment sensor is positioned in a housing of the automatic retention apparatus.

Example 31

An automatic retention system that includes multiple automatic retention apparatuses of any other example, or examples, described herein, the multiple automatic retention apparatuses being optionally mounted to a frame.

Example 32

An automatic retention system according to any other disclosed example, wherein the system includes a frame that defines a joint, and wherein at least one example of a multiple automatic retention apparatus is mounted on one side of the joint, and at least one example of a multiple automatic retention apparatus is mounted on another side of the joint.

Example 33

An automatic retention apparatus of any other example that also includes a control circuit that is configured to increase tension on the retention member according to an adaptive algorithm that automatically adjusts control parameters of the control circuit over time.

Example 34

An automatic retention apparatus of any other example wherein a control circuit a neural network algorithm for adaptively determining values for one or more control parameters of the control circuit based on data stored in a memory.

Example 35

An automatic retention apparatus of any other example wherein the retention member optionally passes through at least a portion of a rotating member of the apparatus.

Glossary of Definitions and Alternatives

While examples are illustrated in the drawings and described herein, this disclosure is to be considered as illustrative and not restrictive in character. The present disclosure is exemplary in nature and all changes, equivalents, and modifications that come within the spirit of the inventions as defined in the claims are included. The detailed description is included herein to discuss aspects of the examples illustrated in the drawings for the purpose of promoting an understanding of the principles of the inventions. No limitation of the scope of the inventions is thereby intended. Any alterations and further modifications in the described examples, and any further applications of the principles described herein are contemplated as would normally occur to one skilled in the art to which the inventions relate. Some examples are disclosed in detail, however some features that may not be relevant may have been left out for the sake of clarity.

Where there are references to publications, patents, and patent applications cited herein, they are understood to be incorporated by reference as if each individual publication, patent, or patent application were specifically and individually indicated to be incorporated by reference and set forth in its entirety herein.

Singular forms “a”, “an”, “the”, and the like include plural referents unless expressly discussed otherwise. As an illustration, references to “a device” or “the device” include one or more of such devices and equivalents thereof.

Directional terms, such as “up”, “down”, “top” “bottom”, “fore”, “aft”, “lateral”, “longitudinal”, “radial”, “circumferential”, etc., are used herein solely for the convenience of the reader in order to aid in the reader’s understanding of the illustrated examples. The use of these directional terms does not in any manner limit the described, illustrated, and/or claimed features to a specific direction and/or orientation.

Multiple related items may be illustrated in the drawings with the same part number but differentiated by a letter for separate individual instances. These may be referred to generally by a distinguishable portion of the full name, and/or by the number alone. For example, if multiple “laterally extending elements” 90A, 90B, 90C, and 90D are illustrated in the drawings, the disclosure may refer to these as “laterally extending elements 90A-90D,” or as “laterally extending elements 90,” or by a distinguishable portion of the full name such as “elements 90”.

The language used in the disclosure are presumed to have only their plain and ordinary meaning, except as explicitly defined below. The words used in the definitions included herein are to only have their plain and ordinary meaning. Such plain and ordinary meaning is inclusive of all consistent dictionary definitions from the most recently published Webster's and Random House dictionaries. As used herein, the following definitions apply to the following terms or to common variations thereof (e.g., singular/plural forms, past/present tenses, etc.):

"About" with reference to numerical values generally refers to plus or minus 10% of the stated value. For example, if the stated value is 4.375, then use of the term "about 4.375" generally means a range between 3.9375 and 4.8125.

"Activate" generally is synonymous with "providing power to", or refers to "enabling a specific function" of a circuit or electronic device that already has power.

"Actuator" generally refers to a device for activating or controlling the actions of an actuated device. This may include, but is not limited to, moving or controlling movement. An actuator may be an element or aspect of the actuated device, such as in the case of a valve that includes an actuator for opening and closing the valve. An actuator may actuate operation of the device by direct mechanical linkage, by signals sent to the device via electromagnetic energy traveling over a wire, optical fiber, or through the air, or by actuating an intervening apparatus that causes the desired actuation of the target device.

"And/or" is inclusive here, meaning "and" as well as "or". For example, "P and/or Q" encompasses, P, Q, and P with Q; and, such "P and/or Q" may include other elements as well.

"Antenna" or "Antenna system" generally refers to an electrical device, or series of devices, in any suitable configuration, that converts electric power into electromagnetic radiation. Such radiation may be either vertically, horizontally, or circularly polarized at any frequency along the electromagnetic spectrum. Antennas transmitting with circular polarity may have either right-handed or left-handed polarization.

In the case of radio waves, an antenna may transmit at frequencies ranging along electromagnetic spectrum from extremely low frequency (ELF) to extremely high frequency (EHF). An antenna or antenna system designed to transmit radio waves may comprise an arrangement of metallic conductors (elements), electrically connected (often through a transmission line) to a receiver or transmitter. An oscillating current of electrons forced through the antenna by a transmitter can create an oscillating magnetic field around the antenna elements, while the charge of the electrons also creates an oscillating electric field along the elements. These time-varying fields radiate away from the antenna into space as a moving transverse electromagnetic field wave. Conversely, during reception, the oscillating electric and magnetic fields of an incoming electromagnetic wave exert force on the electrons in the antenna elements, causing them to move back and forth, creating oscillating currents in the antenna. These currents can then be detected by receivers and processed to retrieve digital or analog signals or data.

Antennas can be designed to transmit and receive radio waves substantially equally in all horizontal directions (omnidirectional antennas), or preferentially in a particular direction (directional or high gain antennas). In the latter case, an antenna may also include additional elements or surfaces which may or may not have any physical electrical connection to the transmitter or receiver. For example, parasitic elements, parabolic reflectors or horns, and other such non-energized elements serve to direct the radio waves into a beam or other desired radiation pattern. Thus antennas may be configured to exhibit increased or decreased directionality or "gain" by the placement of these various surfaces or elements. High gain antennas can be configured to direct a substantially large portion of the radiated electromagnetic energy in a given direction that may be vertical horizontal or any combination thereof.

Antennas may also be configured to radiate electromagnetic energy within a specific range of vertical angles (i.e. "takeoff angles) relative to the earth in order to focus electromagnetic energy toward an upper layer of the atmosphere such as the ionosphere. By directing electromagnetic energy toward the upper atmosphere at a specific angle, specific skip distances may be achieved at particular times of day by transmitting electromagnetic energy at particular frequencies.

Other examples of antennas include emitters and sensors that convert electrical energy into pulses of electromagnetic energy in the visible or invisible light portion of the electromagnetic spectrum. Examples include light emitting diodes, lasers, and the like that are configured to generate electromagnetic energy at frequencies ranging along the electromagnetic spectrum from far infrared to extreme ultraviolet.

"Appendage" generally refers to any portion of the human body. Examples include neck, arm, leg, finger, torso, head, foot etc.

"Battery" generally refers to an electrical energy storage device or storage system including multiple energy storage devices. A battery may include one or more separate electrochemical cells, each converting stored chemical energy into electrical energy by a chemical reaction to generate an electromotive force (or "EMF" measured in Volts). An individual battery cell may have a positive terminal (cathode) with a higher electrical potential, and a negative terminal (anode) that is at a lower electrical potential than the cathode. Any suitable electrochemical cell may be used that employ any suitable chemical process, including galvanic cells, electrolytic cells, fuel cells, flow cells and voltaic piles. When a battery is connected to an external circuit, electrolytes are able to move as ions within the battery, allowing the chemical reactions to be completed at the separate terminals thus delivering energy to the external circuit.

A battery may be a "primary" battery that can produce current immediately upon assembly. Examples of this type include alkaline batteries, nickel oxyhydroxide, lithium-copper, lithium-manganese, lithium-iron, lithium-carbon, lithium-thionyl chloride, mercury oxide, magnesium, zinc-air, zinc-chloride, or zinc-carbon batteries. Such batteries are often referred to as "disposable" insofar as they are generally not rechargeable and are discarded or recycled after discharge.

A battery may also be a "secondary" or "rechargeable" battery that can produce little or no current until charged. Examples of this type include lead-acid batteries, valve regulated lead-acid batteries, sealed gel-cell batteries, and various "dry cell" batteries such as nickel-cadmium (NiCd), nickel-zinc (NiZn), nickel metal hydride (NiMH), and lithium-ion (Li-ion) batteries.

"Braking mechanism" generally refers to a selectively engageable mechanism configured to reduce or halt the movement or rotation of one object with respect to another. In one example, a braking mechanism uses friction between two surfaces selectively pressed together to convert the kinetic energy of the moving or rotating object into heat, though other methods of energy conversion may be employed. Regenerative braking converts much of the energy to electrical energy, which may be stored for later use. Other methods convert kinetic energy into potential energy in such stored forms as pressurized air or pressurized oil. Eddy current brakes use magnetic fields to convert kinetic energy into electric current in the brake disc, fin, or rail, which is converted into heat. Still other braking methods even transform kinetic energy into different forms, for example by transferring the energy to a rotating flywheel.

Another example of a braking mechanism is a ratchet which allows continuous linear or rotary motion in only one direction while preventing motion in the opposite direction. A ratchet may include a series of engagement members such as teeth arranged around a gear or on linear rack. A pivoting, spring-loaded finger called a pawl engages the teeth. The teeth are uniform but asymmetrical, with each tooth having a moderate slope on one edge and a much steeper slope on the other edge. When the teeth are moving in the unrestricted (i.e., forward) direction, the pawl easily slides up and over the gently sloped edges of the teeth, with a biasing element such as a spring forcing it into the depression between the teeth as it passes the tip of each tooth. When the teeth attempt to move in the opposite (backward) direction the pawl catches on the steeply sloped edge of the first tooth it encounters, thereby locking it against the tooth and preventing any further motion in that direction until the pawl is released.

"Cable" generally refers to one or more elongate strands of material that has tensile strength but little if any compressive strength. In other words, a cable is a relatively flexible elongate structure of one or more strands that tends to resist being pulled apart or stretched, but is generally unable to resist being compressed together. Examples include wire rope, flexible shafts, Bowden cables, coaxial cable, twisted pair electrical wire, a single strand of wire, as well as non-wire ropes made of natural or synthetic fibers.

"Controller" generally refers to a mechanical or electronic device configured to control the behavior of another mechanical or electronic device. A controller may include a "control circuit" configured to provide signals or other electrical impulses that may be received and interpreted by the controlled device to indicate how it should behave.

"Computer" generally refers to any computing device configured to compute a result from any number of input values or variables. A computer may include a control circuit for performing calculations to process input or output. A computer may include a memory for storing values to be processed by the processor, or for storing the results of previous processing.

A computer may also be configured to accept input and output from a wide array of input and output devices for receiving or sending values. Such devices include other computers, keyboards, mice, visual displays, printers, industrial equipment, and systems or machinery of all types and sizes. For example, a computer can control a network or network interface to perform various network communications upon request. The network interface may be part of the computer, or characterized as separate and remote from the computer.

A computer may be a single, physical, computing device such as a desktop computer, a laptop computer, or may be composed of multiple devices of the same type such as a group of servers operating as one device in a networked cluster, or a heterogeneous combination of different computing devices operating as one computer and linked together by a communication network. The communication network connected to the computer may also be connected to a wider network such as the internet. Thus a computer may include one or more physical processors or other computing devices or circuitry, and may also include any suitable type of memory.

A computer may also be a virtual computing platform having an unknown or fluctuating number of physical processors and memories or memory devices. A computer may thus be physically located in one geographical location or physically spread across several widely scattered locations with multiple processors linked together by a communication network to operate as a single computer.

The concept of "computer" and "processor" within a computer or computing device also encompasses any such processor or computing device serving to make calculations or comparisons as part of the disclosed system. Processing operations related to threshold comparisons, rules comparisons, calculations, and the like occurring in a computer may occur, for example, on separate servers, the same server with separate processors, or on a virtual computing environment having an unknown number of physical processors as described above.

A computer may be optionally coupled to one or more visual displays and/or may include an integrated visual display. Likewise, displays may be of the same type, or a heterogeneous combination of different visual devices. A computer may also include one or more operator input devices such as a keyboard, mouse, touch screen, laser or infrared pointing device, or gyroscopic pointing device to name just a few representative examples. Also, besides a display, one or more other output devices may be included such as a printer, plotter, industrial manufacturing machine, 3D printer, and the like. As such, various display, input and output device arrangements are possible.

Multiple computers or computing devices may be configured to communicate with one another or with other devices over wired or wireless communication links to form a network. Network communications may pass through various computers operating as network appliances such as switches, routers, firewalls or other network devices or interfaces before passing over other larger computer networks such as the internet. Communications can also be passed over the network as wireless data transmissions carried over electromagnetic waves through transmission lines or free space. Such communications include using WiFi or other Wireless Local Area Network (WLAN) or a cellular transmitter/receiver to transfer data.

"Communication Link" generally refers to a connection between two or more communicating entities and may or may not include a communications channel between the communicating entities. The communication between the communicating entities may occur by any suitable means. For example the connection may be implemented as a physical link, an electrical link, an electromagnetic link, a logical link, or any other suitable linkage facilitating communication.

In the case of physical link, communicating entities may be physically connected one to another. For example, the physical link directly connected to one entity may be directly connected to another. In the case of an electrical link, the communication link may be composed of one or more electrical conductors electrically connected to the communicating entities to form the communication link. In the case of an electromagnetic link, the communicating entities may be coupled to a communications link by sending or receiving electromagnetic energy at any suitable frequency, thus allowing communications to pass as electromagnetic waves. These electromagnetic waves may or may not pass through a physical medium such as a wire or an optical fiber, or through free space, or any combination thereof. Electromagnetic waves may be passed at any suitable frequency including any frequency in the electromagnetic spectrum.

In the case of a logical link, the communication link may be a conceptual linkage between the sender and recipient such as a transmission station and receiving station. Logical link may include any combination of physical, electrical, electromagnetic, or other types of communication links.

"Coupling device" generally refers to a device for coupling one object to another. Examples include a belt buckle, a zipper, a latch, a padlock, a trailer hitch, a clothing button, an electrical connector, boot bindings for a snow board or snow ski, and foot straps for a water ski, kite board, surf board, wave board, or sail board, to name a few non-limiting examples.

"Electrically connected" generally refers to a configuration of two objects that allows electricity to flow between them or through them. In one example, two conductive materials are physically adjacent one another and are sufficiently close together so that electricity can pass between them. In another example, two conductive materials are in physical contact allowing electricity to flow between them.

"Gear" generally refers to a machine part having engagement teeth, or cogs, which extend outwardly away from the body of the gear. The teeth are configured to mesh with another part have corresponding similarly spaced teeth or similarly spaced holes that extend at least a portion of the way through the other part. Types of gears include spur, helical, skew, double helical, bevel, spiral bevel, hypoid, crown, worm, non-circular, rack and pinion, epicyclic, sun and planet, harmonic, cage, cycloidal, and magnetic to name a few nonlimiting examples.

Worm gears resemble screws and mesh with a worm wheel, which looks similar to a spur gear. Worm-and-gear sets are a simple and compact way to achieve a high torque, low speed gear ratio. A worm gear is a species of helical gear, but its helix angle is usually somewhat large (close to 90 degrees) and its body is usually fairly long in the axial direction. These attributes give it screw like qualities. The distinction between a worm and a helical gear is that at least one tooth persists for a full rotation around the helix. A worm gear may be thought of as having a single tooth in the case where the tooth persists for several turns around the helix. A worm gear may also be thought of as having more than one tooth when viewed perpendicular to the long axis of the gear. The reappearing tooth at intervals along the length of the worm may thus be thought of as multiple teeth.

In a worm-and-gear set, the worm can always drive the gear. However, if the gear attempts to drive the worm, it may or may not succeed. Particularly if the lead angle is small, the gear's teeth may simply lock against the worm's teeth, because the force component circumferential to the worm is not sufficient to overcome friction. In traditional music boxes, however, the gear drives the worm, which has a large helix angle. A worm and gear set may be "self-locking", as when it is desired to set the position of a mechanism by turning the worm and then have the mechanism hold that position without allowing retrograde rotation. An example is the machine head found on some types of stringed instruments.

"Hole" generally refers to a hollowed out area defined by a solid body or surface. A hole may extend into the solid body or surface without passing through such as in the case of an indention, depression, or pit. A hole may also pass through one side of an object to another side, thus passing completely through the object. The second side may be the same as the first, such as in the case of loop inside a solid body. Holes may have any suitable shape such as a circle, rectangle, oval, square, triangle, and the like.

"Input" generally refers to something put in, such as a physical substance put in (e.g. increased input of fuel), power or energy put into a machine or system usually with the intent of sizable recovery in the form of output, a component of production (such as land, labor, or raw materials), signals, data, or information fed into a computer, advice or comment, or a stimulus that acts on and is integrated into a bodily system. In the case of information fed into a computer, the input may be generated by a sensor detecting a sense parameter. In this instances, the time-varying values of the sense parameter are at least part of the input.

"Memory" generally refers to any storage system or device configured to retain data or information. Each memory may include one or more types of solid-state electronic memory, magnetic memory, or optical memory, just to name a few. Memory may use any suitable storage technology, or combination of storage technologies, and may be volatile, nonvolatile, or a hybrid combination of volatile and nonvolatile varieties. By way of nonlimiting example, each memory may include solid-state electronic Random Access Memory (RAM), Sequentially Accessible Memory (SAM) (such as the First-In, First-Out (FIFO) variety or the Last-In-First-Out (LIFO) variety), Programmable Read Only Memory (PROM), Electronically Programmable Read Only Memory (EPROM), or Electrically Erasable Programmable Read Only Memory (EEPROM).

Memory can refer to Dynamic Random Access Memory (DRAM) or any variants, including static random access memory (SRAM), Burst SRAM or Synch Burst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (REDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM).

Memory can also refer to non-volatile storage technologies such as non-volatile read access memory (NVRAM), flash memory, non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Domain Wall Memory (DWM) or "Racetrack" memory, Nano-RAM (NRAM), or Millipede memory. Other non-volatile types of memory include optical disc memory (such as a DVD or CD ROM), a magnetically encoded hard disc or hard disc platter, floppy disc, tape, or cartridge media. The concept of a "memory" includes the use of any suitable storage technology or any combination of storage technologies.

"Motor" generally refers to a rotating machine that transforms electrical or chemical energy into mechanical energy, such as by a rotating shaft. Examples include electric motors and internal combustion engines.

"Movement" generally refers to an act of changing physical a physical property such as position, dimension, posture, angle of incidence, or location to name a few nonlimiting examples. Movement of an object may be caused by the object, by the activities of other objects acting on the object either directly or indirectly, and/or by the actions of environmental forces such as gravity, wind, and the like.

"Multiple" as used herein is synonymous with the term "plurality" and refers to more than one, or by extension, two or more.

"Network" or "Computer Network" generally refers to a telecommunications network that allows computers to exchange data. Computers can pass data to each other along data connections by transforming data into a collection of datagrams or packets. The connections between computers and the network may be established using either cables, optical fibers, or via electromagnetic transmissions such as for wireless network devices.

Computers coupled to a network may be referred to as "nodes" or as "hosts" and may originate, broadcast, route, or accept data from the network. Nodes can include any computing device such as personal computers, phones, servers as well as specialized computers that operate to maintain the flow of data across the network, referred to as "network devices". Two nodes can be considered "networked together" when one device is able to exchange information with another device, whether or not they have a direct connection to each other.

Examples of wired network connections may include Digital Subscriber Lines (DSL), coaxial cable lines, or optical fiber lines. The wireless connections may include BLUETOOTH, Worldwide Interoperability for Microwave Access (WiMAX), infrared channel or satellite band, or any wireless local area network (Wi-Fi) such as those implemented using the Institute of Electrical and Electronics Engineers' (IEEE) 802.11 standards (e.g. 802.11(a), 802.11(b), 802.11(g), or 802.11(n) to name a few). Wireless links may also include or use any cellular network standards used to communicate among mobile devices including 1G, 2G, 3G, or 4G. The network standards may qualify as 1G, 2G, etc. by fulfilling a specification or standards such as the specifications maintained by International Telecommunication Union (ITU). For example, a network may be referred to as a "3G network" if it meets the criteria in the International Mobile Telecommunications-2000 (IMT-2000) specification regardless of what it may otherwise be referred to. A network may be referred to as a "4G network" if it meets the requirements of the International Mobile Telecommunications Advanced (IMTAdvanced) specification. Examples of cellular network or other wireless standards include AMPS, GSM, GPRS, UMTS, LTE, LTE Advanced, Mobile WiMAX, and WiMAX-Advanced.

Cellular network standards may use various channel access methods such as FDMA, TDMA, CDMA, or SDMA. Different types of data may be transmitted via different links and standards, or the same types of data may be transmitted via different links and standards.

The geographical scope of the network may vary widely. Examples include a body area network (BAN), a personal area network (PAN), a low power wireless Personal Area Network using IPv6 (6LoWPAN), a local-area network (LAN), a metropolitan area network (MAN), a wide area network (WAN), or the Internet.

A network may have any suitable network topology defining the number and use of the network connections. The network topology may be of any suitable form and may include point-to-point, bus, star, ring, mesh, or tree. A network may be an overlay network which is virtual and is configured as one or more layers that use or "lay on top of" other networks.

A network may utilize different communication protocols or messaging techniques including layers or stacks of protocols. Examples include the Ethernet protocol, the internet protocol suite (TCP/IP), the ATM (Asynchronous Transfer Mode) technique, the SONET (Synchronous Optical Networking) protocol, or the SDE1 (Synchronous Digital Elierarchy) protocol. The TCP/IP internet protocol suite may include application layer, transport layer, internet layer (including, e.g., IPv6), or the link layer.

"Optionally" as used herein means discretionary; not required; possible, but not compulsory; left to personal choice.

"Personal computing device" generally refers to a computing device configured for use by individual people. Examples include mobile devices such as Personal Digital Assistants (PDAs), tablet computers, wearable computers installed in items worn on the human body such as in eye glasses, laptop computers, portable music/video players, computers in automobiles, or cellular telephones such as smart phones. Personal computing devices can be devices that are typically not mobile such as desk top computers, game consoles, or server computers. Personal computing devices may include any suitable input/output devices and may be configured to access a network such as through a wireless or wired connection, and/or via other network hardware.

"Predominately" as used herein is synonymous with greater than 50%.

"Processor" generally refers to one or more electronic components configured to operate as a single unit configured or programmed to process input to generate an output. Alternatively, when of a multi-component form, a processor may have one or more components located remotely relative to the others. One or more components of each processor may be of the electronic variety defining digital circuitry, analog circuitry, or both. In one example, each processor is of a conventional, integrated circuit microprocessor arrangement, such as one or more PENTIUM, i3, i5 or i7 processors supplied by INTEL Corporation of Santa Clara, California, USA. Other examples of commercially available processors include but are not limited to the X8 and Freescale Coldfire processors made by Motorola Corporation of Schaumburg, Illinois, USA; the ARM processor and TEGRA System on a Chip (SoC) processors manufactured by Nvidia of Santa Clara, California, USA; the POWER7 processor manufactured by International Business Machines of White Plains, New York, USA; any of the FX, Phenom, Athlon, Sempron, or Opteron processors manufactured by Advanced Micro Devices of Sunnyvale, California, USA; or the Snapdragon SoC processors manufactured by Qalcomm of San Diego, California, USA.

A processor also includes Application-Specific Integrated Circuit (ASIC). An ASIC is an Integrated Circuit (IC) customized to perform a specific series of logical operations is controlling a computer to perform specific tasks or functions. An ASIC is an example of a processor for a special purpose computer, rather than a processor configured for general-purpose use. An application-specific integrated circuit generally is not reprogrammable to perform other functions and may be programmed once when it is manufactured.

In another example, a processor may be of the "field programmable" type. Such processors may be programmed multiple times "in the field" to perform various specialized or general functions after they are manufactured. A field-programmable processor may include a Field-Programmable Gate Array (FPGA) in an integrated circuit in the processor. FPGA may be programmed to perform a specific series of instructions which may be retained in nonvolatile memory cells in the FPGA. The FPGA may be configured by a customer or a designer using a hardware description language (HDL). In FPGA may be reprogrammed using another computer to reconfigure the FPGA to implement a new set of commands or operating instructions. Such an operation may be executed in any suitable means such as by a firmware upgrade to the processor circuitry.

Just as the concept of a computer is not limited to a single physical device in a single location, so also the concept of a "processor" is not limited to a single physical logic circuit or package of circuits but includes one or more such circuits or circuit packages possibly contained within or across multiple computers in numerous physical locations. In a virtual computing environment, an unknown number of physical processors may be actively processing data, the unknown number may automatically change over time as well.

The concept of a "processor" includes a device configured or programmed to make threshold comparisons, rules comparisons, calculations, or perform logical operations applying a rule to data yielding a logical result (e.g. "true" or "false"). Processing activities may occur in multiple single processors on separate servers, on multiple processors in a single server with separate processors, or on multiple processors physically remote from one another in separate computing devices.

"Portion" means a part of a whole, either separated from or integrated with it.

"Retention Member" generally refers to an element, component, part, piece, or assembly configured to retain a first object in relation to a second object, or to generally apply tension or pressure to an object. The second object may be the retention member itself such as in the case of a retention member whose purpose is to hold itself in position relative to the first object. A retention member may be an assembly of multiple interrelated members that together operate as a retention member such as multiple interrelated segments, strands, or other elements intertwined or otherwise coupled together.

Examples of retention members include, but are not limited to, elongate structures such as a strap, chain, cable, wire, belt, string, and the like. A retention member may include coupling devices such as a snap, latch, coupler, clasp, or hook. Other examples include fasteners such as a screw, bolt, nail, brad, nut, or staple.

"Sense parameter" generally refers to a property of the environment detectable by a sensor. As used herein, sense parameter can be synonymous with an operating condition, environmental factor, sensor parameter, or environmental condition. Sense parameters may include temperature, air pressure, speed, acceleration, tension, weight, force, angle of deflection of an object with respect to another object or with respect to gravity, the presence or intensity of sound or light or other electromagnetic phenomenon, the strength and/or orientation of a magnetic or electrical field, and the like. Other examples include, hear rate, changes in location according to a location service such as the Global Positioning System (GPS), blood pressure, and the like.

"Sensor" generally refers to a transducer configured to sense or detect a characteristic of the environment local to the sensor. For example, sensors may be constructed to detect events or changes in quantities or sense parameters providing a corresponding output, generally as an electrical or electromagnetic signal. A sensor's sensitivity indicates how much the sensor's output changes when the input quantity being measured changes.

"Signal" generally refers to a function or means of representing information. It may be thought of as the output of a transformation or encoding process. The concept generally includes a change in the state of a medium or carrier that conveys the information. The medium can be any suitable medium such as air, water, electricity, magnetism, or electromagnetic energy such as in the case of radio waves, pulses of visible or invisible light, and the like.

As used herein, a "signal" implies a representation of meaningful information. Arbitrary or random changes in the state of a carrier medium are generally not considered "signals" and may be considered "noise". For example, arbitrary binary data streams are not considered as signals. On the other hand, analog and digital signals that are representations of analog physical quantities are examples of signals. A signal is commonly not useful without some way to transmit or send the information, and a receiver responsive to the transmitter for receiving the information.

In a communication system, for example, a transmitter encodes a message to a signal, which is carried to a receiver by the communications channel. For example, the words "The time is 12 o'clock" might be the message spoken into a telephone. The telephone transmitter may then convert the sounds into an electrical voltage signal. The signal is transmitted to the receiving telephone by wires, at the receiver it is reconverted into sounds.

Signals may be thought of as "discrete" or "continuous." Discrete-time signals are often referred to as time series in other fields. Continuous-time signals are often referred to as continuous signals even when the signal functions are not continuous, such as in a square-wave signal.

Another categorization is signals which are "discrete-valued" and "continuous-valued". Particularly in digital signal processing a digital signal is sometimes defined as a sequence of discrete values, that may or may not be derived from an underlying continuous-valued physical process. In other contexts, digital signals are defined as the continuous-time waveform signals in a digital system, representing a bit-stream. In the first case, a signal that is generated by means of a digital modulation method may be considered as converted to an analog signal, while it may be considered as a digital signal in the second case.

"Surround" as used herein means to "extend around at least a portion of" Implicit is a physical or conceptual perimeter around an object that is at least partially enclosed by another object, or arrangement of multiple objects. This includes to fully envelope, to enclose on all sides, and/or to extend fully around the margin or edge. The term may also contemplates intermittent spacing between placement of objects around a portion of another object, such as in the case of chairs that are said to surround a table, or police officers surrounding a building. The term also may be used in the abstract such as when a person's activities are surrounded by secrecy.

What is claimed is:

1. An automatic retention apparatus for automatically adjusting tension on an object, comprising:

a retention member that is separate and distinct from and positionable around the object, the retention member arranged and configured to engage the object to increase or decrease tension on the object, the retention member defining an engagement portion;

a housing separate and distinct from the object, wherein the retention member is mounted to the housing, the housing defining at least one opening through which the engagement portion of the retention member passes into the housing;

an actuator mounted inside the housing that includes a rotating member and a gear mechanism driven by a motor, the gear mechanism including a worm gear with teeth engaging teeth of the rotating member inside the housing, wherein the rotating member is positioned to engage the retention member inside the housing, wherein the engagement portion of the retention member winds and unwinds around the rotating member inside the housing to increase or decrease tension on the object, wherein the rotating member is rotatable around an axis of rotation in a first direction to increase tension on the retention member and in a second direction to decrease tension on the retention member;

at least one sensor arranged and configured to sense changes in a sense parameter associated with the object; and a control circuit responsive to input from the sensor and configured to control the actuator according to the input from the sensor, wherein the control circuit is configured to control the actuator to rotate the rotating member in the first or second direction to adjust tension on the retention member based on input from the sensor.

2. The automatic retention apparatus of claim 1, wherein the rotating member extends out of the housing to engage the retention member, and wherein the retention member is adjacent the housing.

3. The automatic retention apparatus of claim 1, wherein the rotating member includes a worm gear positioned adjacent to the retention member and arranged to engage holes defined in the retention member.

4. The automatic retention apparatus of claim 1, wherein the retention member is rigid and wider than it is thick and defines one or more holes engageable by the worm gear.

5. The automatic retention apparatus of claim 1, wherein the engagement portion comprises a cable coupled to the retention member.

6. The automatic retention apparatus of claim 1, the rotating member includes a shaft and the engagement portion of the retention member winds and unwinds around the shaft to increase or decrease tension on the object.

7. The automatic retention apparatus of claim 1, The retention member includes a flexible substrate having a flat state and a curled state, the curled state of the flexible substrate suitable for conforming to the object.

8. The automatic retention apparatus of claim 7, wherein a first end of the retention member is mounted to the housing, and a second end of the retention member is selectively engageable with the rotating member when the flexible substrate is in the curled state.

9. The automatic retention apparatus of claim 7, wherein an engagement portion of the retention apparatus is configured to automatically engage the rotating member when the retention member is in the curled state.

10. The automatic retention apparatus of claim 7, wherein the control circuit is configured to automatically activate the retention apparatus when the retention member is in the curled state.

11. The automatic retention apparatus of claim 7, wherein the flexible substrate is a metallic bi-stable spring.

12. The automatic retention apparatus of claim 1, comprising:

a frame mounted to the housing; and at least one arm rotatably mounted to the frame;

wherein the retention member is coupled to the at least one arm, wherein the at least one arm is arranged and configured to rotate toward the object with increased tension on the retention member, and wherein the at least one arm is arranged and configured to rotate away from the object with decreased tension on the retention member.

13. The automatic retention apparatus of claim 12, wherein the arm comprises multiple interconnected segments, and wherein the retention member passes through the segments and is mounted to one of the multiple interconnected segments adjacent an end of the arm.

14. The automatic retention apparatus of claim 1, comprising:

a biasing element positioned adjacent to the rotating member, wherein the biasing element is arranged and configured to bias the rotating member in a direction opposite the tension in the retention member.

15. The automatic retention apparatus of claim 14, wherein the biasing element comprises a spring, and wherein the biasing element shares a common shaft with the rotating member.

16. The automatic retention apparatus of claim 1, wherein the rotating member is a first rotating member, the automatic retention apparatus further comprising:

a second rotating member;

wherein the first rotating member is positioned to engage the retention member at a first end;

wherein the second rotating member is positioned to engage the retention member at a second end; and wherein the first and second rotating members are rotatable in a first direction to increase tension on the retention member and in a second direction to decrease tension on the retention member.

17. The automatic retention apparatus of claim 1, wherein the object is a human or animal appendage, and wherein the sense parameter is any combination of blood pressure, body temperature, blood oxygen level, or heart rate.

18. The automatic retention apparatus of claim 17, wherein the control circuit is configured to increase tension on the retention member when the sense parameter matches a first target criteria, and wherein the control circuit is configured to decrease tension on the retention member when the sense parameter matches a second target criteria.

19. The automatic retention apparatus of claim 1, comprising:

an environment sensor arranged and configured to sense changes in an environmental sense parameter associated with an environment surrounding the sensor, wherein the control circuit is responsive to the environmental sense parameter that includes any combination of speed, angular momentum, velocity, movement, or acceleration.

20. The automatic retention apparatus of claim 18, wherein the environment sensor is positioned in the housing.

* * * * *